US008038708B2

(12) United States Patent
Case et al.

(10) Patent No.: US 8,038,708 B2
(45) Date of Patent: Oct. 18, 2011

(54) IMPLANTABLE DEVICE WITH REMODELABLE MATERIAL AND COVERING MATERIAL

(75) Inventors: Brian C. Case, Lake Villa, IL (US); Charles W. Agnew, West Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 425 days.

(21) Appl. No.: 11/640,674

(22) Filed: Dec. 18, 2006

(65) Prior Publication Data
US 2007/0162103 A1 Jul. 12, 2007

Related U.S. Application Data

(60) Provisional application No. 60/753,902, filed on Dec. 23, 2005.

(51) Int. Cl.
*A61F 2/06* (2006.01)
(52) U.S. Cl. ...................................... 623/1.24
(58) Field of Classification Search ............... 623/2.11, 623/2.12, 2.13, 2.18, 1.24, 1.26, 1.11–1.17, 623/2.14, 23.64, 23.65, 23.66, 23.68, 23.7; 606/108, 194, 8
See application file for complete search history.

(56) References Cited

U.S. PATENT DOCUMENTS

| | | |
|---|---|---|
| 3,736,598 A | 6/1973 | Bellhouse et al. |
| 4,086,665 A * | 5/1978 | Poirier .......................... 623/1.44 |
| 4,297,749 A | 11/1981 | Davis et al. |
| 4,306,319 A | 12/1981 | Kaster ................................. 3/1.5 |
| 4,441,216 A | 4/1984 | Ionescu et al. |
| 4,597,767 A | 7/1986 | Lenkei ................................. 623/2 |
| 4,605,408 A | 8/1986 | Carpentier ......................... 623/2 |
| 4,692,165 A | 9/1987 | Bokros ................................ 623/2 |
| 4,950,287 A | 8/1990 | Reif .................................... 623/2 |
| 5,037,434 A | 8/1991 | Lane ................................... 623/2 |
| 5,064,432 A | 11/1991 | Reif .................................... 623/2 |
| 5,123,919 A | 6/1992 | Sauter et al. ....................... 623/2 |
| 5,139,515 A | 8/1992 | Robicsek |
| 5,197,979 A | 3/1993 | Quintero et al. |
| 5,336,615 A | 8/1994 | Bell et al. ................... 435/240.2 |
| 5,344,426 A | 9/1994 | Lau et al. |
| 5,358,518 A | 10/1994 | Camilli ............................. 623/2 |

(Continued)

FOREIGN PATENT DOCUMENTS

EP 0850607 7/1998

(Continued)

OTHER PUBLICATIONS

European Search Report and Search Opinion, issued by the European Patent Office, Nov. 9, 2009 for Application No. 09170581.4-2320.

(Continued)

*Primary Examiner* — Alvin J Stewart
(74) *Attorney, Agent, or Firm* — Buchanan Nipper

(57) ABSTRACT

Medical devices for implantation within a body vessel can include a remodelable material, such as an extracellular matrix material, positioned within a lumen defined by an outer covering material. The covering material is preferably substantially non-remodelable, and can be supported by a radially expandable frame. The medical device can also include a valve means positioned within the covering material. The valve means can include one or more valve leaflets formed from the remodelable material, and a separate valve support frame. One or more therapeutic agents can be associated with the remodelable material or the covering material.

15 Claims, 7 Drawing Sheets

U.S. PATENT DOCUMENTS

| | | | |
|---|---|---|---|
| 5,397,346 | A | 3/1995 | Walker et al. .................... 623/2 |
| 5,397,355 | A | 3/1995 | Marin et al. |
| 5,411,552 | A | 5/1995 | Andersen et al. ................. 623/2 |
| 5,413,599 | A | 5/1995 | Imachi et al. .................... 623/2 |
| 5,500,014 | A | 3/1996 | Quijano et al. ................... 623/2 |
| 5,545,215 | A | 8/1996 | Duran |
| 5,591,197 | A | 1/1997 | Orth et al. |
| 5,607,465 | A | 3/1997 | Camilli ............................ 623/1 |
| 5,609,598 | A | 3/1997 | Laufer et al. .................. 606/142 |
| 5,609,629 | A | 3/1997 | Fearnot et al. ................... 623/1 |
| 5,693,085 | A * | 12/1997 | Buirge et al. ................. 623/1.13 |
| 5,709,707 | A | 1/1998 | Lock et al. |
| 5,713,953 | A | 2/1998 | Vallana et al. |
| 5,728,152 | A | 3/1998 | Mirsch, II et al. ................ 623/2 |
| 5,733,325 | A | 3/1998 | Robinson et al. |
| 5,755,781 | A | 5/1998 | Jayaraman |
| 5,824,045 | A | 10/1998 | Alt |
| 5,824,049 | A | 10/1998 | Ragheb et al. .................... 623/1 |
| 5,824,069 | A | 10/1998 | Lemole ............................ 623/2 |
| 5,836,964 | A | 11/1998 | Richter et al. |
| 5,840,081 | A * | 11/1998 | Andersen et al. ............ 623/1.11 |
| 5,843,117 | A | 12/1998 | Alt et al. |
| 5,855,600 | A | 1/1999 | Alt |
| 5,855,601 | A | 1/1999 | Bessler et al. .................... 623/2 |
| 5,873,904 | A | 2/1999 | Ragheb et al. .................... 623/1 |
| 5,876,445 | A | 3/1999 | Andersen et al. |
| 5,879,382 | A | 3/1999 | Boneau |
| 5,895,420 | A | 4/1999 | Mirsch, II et al. ................ 623/2 |
| 5,899,935 | A | 5/1999 | Ding ............................... 623/1 |
| 5,907,893 | A | 6/1999 | Zadno-Azizi et al. |
| 5,911,732 | A | 6/1999 | Hojeibane |
| 5,938,682 | A | 8/1999 | Hojeibane et al. |
| 5,954,766 | A | 9/1999 | Zadno-Azizi et al. ............. 623/2 |
| 5,957,949 | A * | 9/1999 | Leonhardt et al. ........... 623/1.24 |
| 5,980,551 | A | 11/1999 | Summers et al. ............. 606/194 |
| 6,015,431 | A | 1/2000 | Thornton et al. ................. 623/1 |
| 6,017,363 | A | 1/2000 | Hojeibane |
| 6,033,398 | A | 3/2000 | Farley et al. |
| 6,053,940 | A | 4/2000 | Wijay |
| 6,096,070 | A | 8/2000 | Ragheb et al. .................... 623/1 |
| 6,100,443 | A | 8/2000 | Sims et al. ...................... 800/14 |
| 6,106,550 | A | 8/2000 | Magovern et al. ........... 623/2.38 |
| 6,123,721 | A | 9/2000 | Jang |
| 6,126,686 | A | 10/2000 | Badylak et al. ............. 623/1.24 |
| 6,129,755 | A | 10/2000 | Mathis et al. |
| 6,132,460 | A | 10/2000 | Thompson |
| 6,132,461 | A | 10/2000 | Thompson |
| 6,146,416 | A | 11/2000 | Andersen et al. |
| 6,159,237 | A | 12/2000 | Alt et al. |
| 6,190,406 | B1 | 2/2001 | Duerig et al. |
| 6,200,336 | B1 | 3/2001 | Pavcnik et al. |
| 6,235,053 | B1 | 5/2001 | Jang |
| 6,238,409 | B1 | 5/2001 | Hojeibane |
| 6,238,872 | B1 | 5/2001 | Mosseri ......................... 435/7.1 |
| 6,241,763 | B1 | 6/2001 | Drasler et al. ............... 623/1.24 |
| 6,241,765 | B1 | 6/2001 | Griffin et al. ................ 623/2.38 |
| 6,254,564 | B1 * | 7/2001 | Wilk et al. ....................... 604/9 |
| 6,254,632 | B1 | 7/2001 | Wu et al. ...................... 623/1.15 |
| 6,255,277 | B1 | 7/2001 | Stamler et al. ................... 514/2 |
| 6,258,116 | B1 | 7/2001 | Hojeibane |
| 6,280,467 | B1 | 8/2001 | Leonhardt |
| 6,283,990 | B1 | 9/2001 | Kanesaka |
| 6,287,334 | B1 | 9/2001 | Moll et al. .................... 623/1.24 |
| 6,287,339 | B1 | 9/2001 | Vazquez et al. ............... 623/2.4 |
| 6,290,729 | B1 | 9/2001 | Slepian et al. .............. 623/23.72 |
| 6,299,637 | B1 | 10/2001 | Shaolian et al. ............. 623/1.24 |
| 6,302,917 | B1 * | 10/2001 | Dua et al. .................... 623/23.68 |
| 6,312,459 | B1 | 11/2001 | Huang et al. |
| 6,312,465 | B1 | 11/2001 | Griffin et al. |
| 6,315,793 | B1 | 11/2001 | Bokros et al. |
| 6,325,819 | B1 | 12/2001 | Pavcnik et al. |
| 6,328,763 | B1 | 12/2001 | Love et al. |
| 6,338,730 | B1 | 1/2002 | Carpentier |
| 6,340,366 | B2 | 1/2002 | Wijay |
| 6,342,067 | B1 | 1/2002 | Mathis et al. |
| 6,342,070 | B1 | 1/2002 | Nguyen-Thien-Nhon |
| 6,348,065 | B1 | 2/2002 | Brown et al. |
| 6,352,554 | B2 | 3/2002 | De Paulis |
| 6,355,056 | B1 | 3/2002 | Pinheiro |
| 6,425,916 | B1 * | 7/2002 | Garrison et al. ............. 623/2.11 |
| 6,436,104 | B2 | 8/2002 | Hojeibane |
| 6,440,163 | B1 | 8/2002 | Swanson et al. |
| 6,440,164 | B1 | 8/2002 | DiMatteo et al. ........... 623/1.24 |
| 6,451,044 | B1 | 9/2002 | Naghavi et al. ................ 607/96 |
| 6,458,153 | B1 * | 10/2002 | Bailey et al. ................ 623/1.24 |
| 6,471,723 | B1 | 10/2002 | Ashworth et al. ........... 623/2.42 |
| 6,475,232 | B1 | 11/2002 | Babbs et al. ................. 623/1.13 |
| 6,488,702 | B1 | 12/2002 | Besselink |
| 6,494,909 | B2 | 12/2002 | Greenhalgh ................. 623/1.24 |
| 6,503,272 | B2 | 1/2003 | Duerig et al. ................ 623/1.24 |
| 6,508,833 | B2 | 1/2003 | Pavcnik et al. |
| 6,514,063 | B2 | 2/2003 | Acciai et al. |
| 6,530,951 | B1 | 3/2003 | Bates et al. .................. 623/1.45 |
| 6,544,291 | B2 * | 4/2003 | Taylor ........................ 623/23.68 |
| 6,558,415 | B2 | 5/2003 | Thompson |
| 6,562,063 | B1 | 5/2003 | Euteneuer et al. ........... 623/1.12 |
| 6,565,600 | B2 | 5/2003 | Hojeibane |
| 6,572,650 | B1 | 6/2003 | Abraham et al. ............ 623/1.38 |
| 6,582,462 | B1 * | 6/2003 | Andersen et al. ............ 623/1.26 |
| 6,585,765 | B1 | 7/2003 | Hossainy et al. ............ 623/1.45 |
| 6,598,307 | B2 | 7/2003 | Love et al. |
| 6,613,086 | B1 | 9/2003 | Moe et al. |
| 6,616,699 | B2 | 9/2003 | Zilla et al. ..................... 623/901 |
| 6,638,303 | B1 | 10/2003 | Campbell ...................... 623/2.2 |
| 6,652,578 | B2 * | 11/2003 | Bailey et al. ................ 623/1.24 |
| 6,663,661 | B2 | 12/2003 | Boneau |
| 6,669,724 | B2 | 12/2003 | Park et al. |
| 6,676,698 | B2 | 1/2004 | McGuckin, Jr. et al. .... 623/1.24 |
| 6,678,962 | B1 | 1/2004 | Love et al. |
| 6,685,739 | B2 | 2/2004 | DiMatteo et al. ........... 623/1.24 |
| 6,702,848 | B1 | 3/2004 | Zilla et al. ................... 623/1.39 |
| 6,716,241 | B2 | 4/2004 | Wilder et al. ............... 623/1.24 |
| 6,726,718 | B1 | 4/2004 | Carlyle et al. ............... 623/2.42 |
| 6,730,117 | B1 | 5/2004 | Tseng et al. |
| 6,746,476 | B1 | 6/2004 | Hojeibane |
| 6,752,828 | B2 | 6/2004 | Thornton ..................... 623/1.24 |
| 6,780,849 | B2 | 8/2004 | Herrmann et al. .............. 514/23 |
| 6,783,793 | B1 | 8/2004 | Hossainy et al. ............ 427/2.25 |
| 6,786,922 | B2 | 9/2004 | Schaeffer |
| 6,790,237 | B2 | 9/2004 | Stinson |
| 6,821,292 | B2 | 11/2004 | Pazienza et al. |
| 6,837,903 | B2 | 1/2005 | Vyavahare et al. .......... 623/2.42 |
| 6,852,122 | B2 | 2/2005 | Rush ........................... 623/1.13 |
| 6,878,162 | B2 | 4/2005 | Bales et al. |
| 6,894,154 | B2 | 5/2005 | Nabel et al. .................. 536/23.2 |
| 6,939,369 | B2 | 9/2005 | Osborne et al. ............. 623/1.11 |
| 6,955,686 | B2 | 10/2005 | Majercak et al. |
| 6,958,076 | B2 | 10/2005 | Acosta et al. ............... 623/1.24 |
| 6,962,603 | B1 | 11/2005 | Brown et al. |
| 6,966,923 | B2 | 11/2005 | Gittings ........................ 623/1.2 |
| 6,969,400 | B2 | 11/2005 | Rhee et al. ...................... 623/1 |
| 6,974,474 | B2 | 12/2005 | Pavcnik et al. |
| 6,976,996 | B1 | 12/2005 | Mathis et al. |
| 6,986,735 | B2 | 1/2006 | Abraham et al. ............... 600/36 |
| 7,018,402 | B2 | 3/2006 | Vito et al. .................... 623/1.15 |
| 7,018,403 | B1 | 3/2006 | Pienknagura |
| 7,018,404 | B2 | 3/2006 | Holmberg et al. |
| 7,018,406 | B2 | 3/2006 | Seguin et al. |
| 7,025,777 | B2 | 4/2006 | Moore |
| 7,025,780 | B2 | 4/2006 | Gabbay |
| 7,029,493 | B2 | 4/2006 | Majercak et al. |
| 7,041,131 | B2 | 5/2006 | Abraham et al. ............ 623/1.47 |
| 7,044,966 | B2 | 5/2006 | Svanidze |
| 7,060,088 | B1 | 6/2006 | Fischell et al. |
| 7,070,616 | B2 | 7/2006 | Majercak et al. |
| 7,087,089 | B2 | 8/2006 | Patel et al. .................. 623/23.72 |
| 7,101,396 | B2 | 9/2006 | Artof et al. |
| 7,105,019 | B2 | 9/2006 | Hojeibane |
| 7,118,600 | B2 | 10/2006 | Dua et al. |
| 7,125,418 | B2 | 10/2006 | Duran et al. |
| 7,128,756 | B2 | 10/2006 | Lowe et al. |
| 7,128,759 | B2 | 10/2006 | Osborne et al. ............. 623/1.24 |
| 7,147,661 | B2 | 12/2006 | Chobotov et al. |
| 7,153,324 | B2 | 12/2006 | Case et al. |
| 7,160,320 | B2 | 1/2007 | Duran |
| 7,160,592 | B2 | 1/2007 | Rypacek et al. .............. 428/36.9 |
| 7,175,652 | B2 | 2/2007 | Cook et al. .................. 623/1.13 |

| | | |
|---|---|---|
| 7,195,641 B2 | 3/2007 | Palmaz et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,354,455 B2 | 4/2008 | Stinson |
| 7,377,938 B2 | 5/2008 | Sarac et al. |
| 7,381,219 B2 | 6/2008 | Salahieh et al. |
| 7,445,631 B2 | 11/2008 | Salahieh et al. |
| 7,452,371 B2 | 11/2008 | Pavcnik et al. |
| 7,524,331 B2 | 4/2009 | Birdsall |
| 7,544,207 B2 | 6/2009 | Osborne et al. |
| 7,547,322 B2 | 6/2009 | Sarac et al. |
| 7,594,927 B2 | 9/2009 | Majercak et al. |
| 7,625,399 B2 | 12/2009 | Case et al. |
| 2001/0002444 A1 | 5/2001 | Zilla et al. ............... 623/1.39 |
| 2001/0016770 A1 | 8/2001 | Allen et al. |
| 2001/0018610 A1 | 8/2001 | Limon |
| 2001/0020183 A1 | 9/2001 | Jang |
| 2001/0039450 A1 | 11/2001 | Pavcnik et al. ........... 623/1.24 |
| 2001/0041928 A1 | 11/2001 | Pavcnik et al. ........... 623/1.13 |
| 2001/0049553 A1 | 12/2001 | De Paulis |
| 2002/0010504 A1 | 1/2002 | Alt |
| 2002/0026236 A1 | 2/2002 | Helmus et al. ........... 623/1.42 |
| 2002/0058994 A1 | 5/2002 | Hill et al. ................ 623/2.11 |
| 2002/0065546 A1 | 5/2002 | Machan et al. ........... 623/1.13 |
| 2002/0082679 A1 | 6/2002 | Sirhan et al. ............. 623/1.15 |
| 2002/0091444 A1 | 7/2002 | Yang ...................... 623/11.11 |
| 2002/0099439 A1 | 7/2002 | Schwartz et al. |
| 2002/0111339 A1 | 8/2002 | Klausener et al. |
| 2002/0123790 A1 | 9/2002 | White et al. |
| 2002/0129820 A1 | 9/2002 | Ryan et al. |
| 2002/0133183 A1 | 9/2002 | Lentz et al. ............... 606/155 |
| 2002/0133223 A1 | 9/2002 | Vito et al. ................ 623/1.18 |
| 2002/0177894 A1 | 11/2002 | Acosta et al. |
| 2002/0183857 A1 | 12/2002 | Yang ...................... 623/23.72 |
| 2002/0193871 A1 | 12/2002 | Beyersdorf et al. |
| 2003/0014126 A1 | 1/2003 | Patel et al. ............... 623/23.72 |
| 2003/0040792 A1* | 2/2003 | Gabbay .................... 623/2.11 |
| 2003/0060875 A1 | 3/2003 | Wittens .................... 623/1.13 |
| 2003/0065377 A1 | 4/2003 | Davila et al. ............. 623/1.13 |
| 2003/0065379 A1 | 4/2003 | Babbs et al. ............. 623/1.13 |
| 2003/0069646 A1 | 4/2003 | Stinson |
| 2003/0082148 A1 | 5/2003 | Ludwig et al. .............. 424/93.7 |
| 2003/0093144 A1 | 5/2003 | Jang |
| 2003/0093147 A1 | 5/2003 | Ogle et al. ................ 623/2.12 |
| 2003/0109922 A1 | 6/2003 | Peterson et al. |
| 2003/0114919 A1 | 6/2003 | McQuiston et al. |
| 2003/0130726 A1 | 7/2003 | Thorpe et al. ........... 623/1.24 |
| 2003/0130746 A1 | 7/2003 | Ashworth et al. ........ 623/23.72 |
| 2003/0139805 A1 | 7/2003 | Holmberg et al. |
| 2003/0144670 A1 | 7/2003 | Pavcnik et al. ............ 606/108 |
| 2003/0149477 A1* | 8/2003 | Gabbay .................... 623/2.14 |
| 2003/0167088 A1 | 9/2003 | Abraham et al. ......... 623/1.41 |
| 2003/0171801 A1 | 9/2003 | Bates ....................... 623/1.13 |
| 2003/0171824 A1 | 9/2003 | Abraham et al. ......... 623/23.75 |
| 2003/0176914 A1 | 9/2003 | Rabkin et al. |
| 2003/0181976 A1 | 9/2003 | Vyavahare et al. ........ 623/2.42 |
| 2003/0187500 A1 | 10/2003 | Jansen et al. |
| 2003/0190406 A1 | 10/2003 | Hossainy et al. ........... 427/2.25 |
| 2003/0191517 A1 | 10/2003 | Osborne et al. .......... 623/1.13 |
| 2003/0195618 A1 | 10/2003 | Abraham et al. ......... 623/1.41 |
| 2003/0199967 A1 | 10/2003 | Hartley et al. ............ 623/1.13 |
| 2003/0208261 A1 | 11/2003 | Thorpe et al. |
| 2003/0209835 A1 | 11/2003 | Chun et al. ................... 264/339 |
| 2003/0220683 A1 | 11/2003 | Minasian et al. |
| 2003/0229363 A1 | 12/2003 | Sharkawy et al. .......... 606/153 |
| 2003/0236568 A1 | 12/2003 | Hojeibane et al. |
| 2004/0006383 A1 | 1/2004 | Zilla et al. ................ 623/1.39 |
| 2004/0019374 A1 | 1/2004 | Hojeibane et al. |
| 2004/0024444 A1 | 2/2004 | Moore |
| 2004/0024447 A1 | 2/2004 | Haverich |
| 2004/0039441 A1 | 2/2004 | Rowland et al. ........... 623/1.42 |
| 2004/0044401 A1 | 3/2004 | Bales et al. |
| 2004/0054396 A1 | 3/2004 | Hartley et al. ........... 623/1.13 |
| 2004/0082989 A1 | 4/2004 | Cook et al. ............... 623/1.13 |
| 2004/0093061 A1 | 5/2004 | Acosta et al. |
| 2004/0093070 A1 | 5/2004 | Hojeibane et al. |
| 2004/0093073 A1 | 5/2004 | Lowe et al. |
| 2004/0102834 A1 | 5/2004 | Nakano et al. |
| 2004/0106985 A1 | 6/2004 | Jang |
| 2004/0117004 A1 | 6/2004 | Osborne et al. ........... 623/1.36 |
| 2004/0147997 A1 | 7/2004 | Gittings ................... 623/1.11 |
| 2004/0148010 A1 | 7/2004 | Rush ....................... 623/1.13 |
| 2004/0167619 A1 | 8/2004 | Case et al. ................ 623/1.34 |
| 2004/0176832 A1 | 9/2004 | Hartley et al. ............ 623/1.11 |
| 2004/0176833 A1 | 9/2004 | Pavcnik et al. ............ 623/1.13 |
| 2004/0199241 A1 | 10/2004 | Gravett et al. ........... 623/1.13 |
| 2004/0210301 A1 | 10/2004 | Obermiller ................ 623/1.24 |
| 2004/0215333 A1 | 10/2004 | Duran et al. |
| 2004/0215338 A1 | 10/2004 | Elkins et al. ............. 623/1.46 |
| 2004/0225348 A1 | 11/2004 | Case et al. ................ 623/1.15 |
| 2004/0236411 A1* | 11/2004 | Sarac et al. ............... 623/1.26 |
| 2004/0243218 A1 | 12/2004 | Schaeffer |
| 2004/0243222 A1 | 12/2004 | Osborne et al. ........... 623/1.24 |
| 2004/0254629 A1 | 12/2004 | Fernandes et al. ......... 623/1.13 |
| 2004/0254640 A1 | 12/2004 | Sutherland et al. |
| 2004/0260318 A1 | 12/2004 | Hunter et al. ............. 606/153 |
| 2004/0260389 A1 | 12/2004 | Case et al. ............... 623/1.24 |
| 2004/0267354 A1 | 12/2004 | Ringeisen et al. ......... 623/1.42 |
| 2005/0021126 A1 | 1/2005 | Machan et al. ........... 623/1.13 |
| 2005/0027348 A1 | 2/2005 | Case et al. ............... 623/1.24 |
| 2005/0038455 A1 | 2/2005 | Bates et al. ............... 606/153 |
| 2005/0038499 A1 | 2/2005 | Nabel et al. ............. 623/1.15 |
| 2005/0043786 A1 | 2/2005 | Chu et al. ................. 623/1.42 |
| 2005/0055079 A1 | 3/2005 | Duran |
| 2005/0055082 A1 | 3/2005 | Muvhar et al. ............ 623/1.15 |
| 2005/0059923 A1 | 3/2005 | Gamboa |
| 2005/0065593 A1 | 3/2005 | Chu et al. ................. 623/1.15 |
| 2005/0075713 A1 | 4/2005 | Biancucci et al. |
| 2005/0085900 A1 | 4/2005 | Case et al. ............... 623/1.24 |
| 2005/0085901 A1 | 4/2005 | Castro et al. ............ 623/1.39 |
| 2005/0085902 A1 | 4/2005 | Wright et al. ............ 623/1.46 |
| 2005/0096735 A1 | 5/2005 | Hojeibane et al. |
| 2005/0102021 A1 | 5/2005 | Osborne .................. 623/1.13 |
| 2005/0107862 A1 | 5/2005 | Ohlenschlaeger ........... 623/1.11 |
| 2005/0125054 A1 | 6/2005 | Bhat et al. ............... 623/1.42 |
| 2005/0131517 A1 | 6/2005 | Hartley et al. ............ 623/1.13 |
| 2005/0131518 A1 | 6/2005 | Hartley et al. ............ 623/1.13 |
| 2005/0131519 A1 | 6/2005 | Hartley ................... 623/1.13 |
| 2005/0131525 A1 | 6/2005 | Hartley ................... 623/1.15 |
| 2005/0131531 A1 | 6/2005 | Keenan .................. 623/1.39 |
| 2005/0137677 A1 | 6/2005 | Rush ...................... 623/1.13 |
| 2005/0143807 A1 | 6/2005 | Pavcnik et al. ........... 623/1.24 |
| 2005/0143810 A1* | 6/2005 | Dauner et al. ............. 623/2.12 |
| 2005/0143817 A1 | 6/2005 | Hunter et al. ............. 623/11.11 |
| 2005/0149167 A1 | 7/2005 | Osborne et al. ........... 623/1.13 |
| 2005/0149167 A1 | 7/2005 | Hunter et al. ............. 623/1.42 |
| 2005/0154445 A1 | 7/2005 | Hunter et al. ............. 623/1.13 |
| 2005/0154454 A1 | 7/2005 | Hunter et al. ............. 623/1.42 |
| 2005/0158360 A1 | 7/2005 | Falotico et al. ............ 424/424 |
| 2005/0159803 A1 | 7/2005 | Lad et al. ................ 623/1.13 |
| 2005/0159806 A1 | 7/2005 | Lad et al. ................ 623/1.41 |
| 2005/0165467 A1 | 7/2005 | Hunter et al. ............. 623/1.13 |
| 2005/0165488 A1 | 7/2005 | Hunter et al. ............. 623/17.16 |
| 2005/1014916 | 7/2005 | Schaeffer et al. .......... 623/1.13 |
| 2005/0171594 A1 | 8/2005 | Machan et al. ........... 623/1.13 |
| 2005/0171597 A1 | 8/2005 | Boatman et al. .......... 623/1.22 |
| 2005/0171598 A1 | 8/2005 | Schaeffer ................. 623/1.35 |
| 2005/0177222 A1 | 8/2005 | Mead ..................... 623/1.13 |
| 2005/0177225 A1 | 8/2005 | Hunter et al. ............. 623/1.42 |
| 2005/0181011 A1 | 8/2005 | Hunter et al. ............. 424/423 |
| 2005/0181977 A1 | 8/2005 | Hunter et al. ............. 514/2 |
| 2005/0182483 A1* | 8/2005 | Osborne et al. ........... 623/1.24 |
| 2005/0182485 A1 | 8/2005 | Falotico et al. ........... 623/1.42 |
| 2005/0187140 A1 | 8/2005 | Hunter et al. ............. 514/2 |
| 2005/0187604 A1* | 8/2005 | Eells et al. ............... 623/1.13 |
| 2005/0187608 A1 | 8/2005 | O'Hara .................. 623/1.15 |
| 2005/0192606 A1 | 9/2005 | Paul, Jr. et al. ............. 606/159 |
| 2005/0208099 A1 | 9/2005 | Caplice et al. ............. 424/423 |
| 2005/0208100 A1 | 9/2005 | Weber et al. .............. 424/426 |
| 2005/0209688 A1 | 9/2005 | Falotico et al. ........... 623/1.42 |
| 2005/0216077 A1 | 9/2005 | Mathis et al. |
| 2005/0222661 A1 | 10/2005 | Case et al. ............... 623/1.1 |
| 2005/0222668 A1 | 10/2005 | Schaeffer et al. .......... 623/1.13 |
| 2005/0222669 A1 | 10/2005 | Purdy .................... 623/1.13 |
| 2005/0222674 A1* | 10/2005 | Paine ..................... 623/1.24 |
| 2005/0228472 A1 | 10/2005 | Case et al. ............... 623/1.1 |
| 2005/0228479 A1 | 10/2005 | Pavcnik et al. ........... 623/1.11 |

| | | | | | |
|---|---|---|---|---|---|
| 2005/0228486 A1 | 10/2005 | Case et al. ............... 623/1.24 | 2006/0210959 A1 | 9/2006 | Dancu et al. ............... 435/1.2 |
| 2005/0234541 A1 | 10/2005 | Hunt et al. ............... 623/1.24 | 2006/0217800 A1 | 9/2006 | Ganesan ..................... 623/1.46 |
| 2005/0234542 A1 | 10/2005 | Melsheimer ............. 623/1.35 | 2006/0228391 A1 | 10/2006 | Seyedin et al. ............. 424/422 |
| 2005/0234546 A1 | 10/2005 | Nugent et al. | 2006/0233855 A1 | 10/2006 | Seliktar et al. ............. 424/422 |
| 2005/0244460 A1 | 11/2005 | Alferiev et al. ............. 424/426 | 2006/0241744 A1 | 10/2006 | Beith |
| 2005/0256588 A1 | 11/2005 | Sawa et al. ............... 623/23.72 | 2006/0259122 A1 | 11/2006 | Eliseev ..................... 623/1.12 |
| 2005/0267560 A1 | 12/2005 | Bates ........................ 623/1.1 | 2006/0271159 A1 | 11/2006 | Gregorich et al. |
| 2005/0273155 A1 | 12/2005 | Bahler et al. .............. 623/1.13 | 2006/0271162 A1 | 11/2006 | Vito et al. ................. 623/1.15 |
| 2005/0283224 A1 | 12/2005 | King ......................... 623/1.13 | 2006/0276882 A1 | 12/2006 | Case et al. |
| 2006/0004433 A1 | 1/2006 | Greenberg et al. ........ 623/1.11 | 2006/0276883 A1 | 12/2006 | Greenberg et al. ........ 623/1.31 |
| 2006/0009835 A1 | 1/2006 | Osborne et al. ............ 623/1.13 | 2006/0281966 A1 | 12/2006 | Peacock, III ................ 600/37 |
| 2006/0009839 A1 | 1/2006 | Tan ............................ 623/1.38 | 2006/0287717 A1 | 12/2006 | Rowe et al. |
| 2006/0015178 A1 | 1/2006 | Moaddeb et al. | 2007/0003588 A1 | 1/2007 | Chinn et al. ............... 424/423 |
| 2006/0020324 A1 | 1/2006 | Schmid et al. ............. 623/1.16 | 2007/0003599 A1 | 1/2007 | Schwarz ..................... 424/426 |
| 2006/0020328 A1 | 1/2006 | Tan ............................ 623/1.42 | 2007/0021822 A1 | 1/2007 | Boatman ..................... 623/1.13 |
| 2006/0041182 A1 | 2/2006 | Forbes et al. ............... 600/12 | 2007/0027526 A1 | 2/2007 | Demetriades et al. ...... 623/1.13 |
| 2006/0058864 A1 | 3/2006 | Schaeffer et al. .......... 623/1.11 | 2007/0037283 A1 | 2/2007 | Patel et al. .................. 435/380 |
| 2006/0074480 A1 | 4/2006 | Bales et al. | 2007/0038291 A1 | 2/2007 | Case et al. |
| 2006/0085060 A1* | 4/2006 | Campbell .................. 623/1.26 | 2007/0043428 A1 | 2/2007 | Jennings et al. ............ 623/1.15 |
| 2006/0100717 A1 | 5/2006 | Abraham et al. ........... 623/917 | 2007/0260327 A1 | 11/2007 | Case et al. |
| 2006/0106455 A1 | 5/2006 | Furst et al. .................. 623/1.31 | 2008/0082166 A1 | 4/2008 | Styrc et al. |
| 2006/0111770 A1 | 5/2006 | Pavcnik et al. .............. 623/1.13 | 2008/0249619 A1 | 10/2008 | Stacchino et al. |
| 2006/0116572 A1 | 6/2006 | Case | 2009/0082858 A1 | 3/2009 | Nugent et al. |
| 2006/0118189 A1 | 6/2006 | Tekulve et al. ............. 137/846 | 2009/0088836 A1 | 4/2009 | Bishop et al. |
| 2006/0129225 A1 | 6/2006 | Kopia et al. ................ 623/1.13 | 2009/0099653 A1 | 4/2009 | Suri et al. |
| 2006/0134218 A1 | 6/2006 | Abul-Khoudoud et al. .. 424/486 | 2009/0240320 A1 | 9/2009 | Tuval et al. |
| 2006/0136044 A1 | 6/2006 | Osborne et al. ............. 623/1.24 | 2009/0248132 A1 | 10/2009 | Bloom et al. |
| 2006/0136045 A1 | 6/2006 | Flagle et al. | 2009/0270965 A1 | 10/2009 | Sinha et al. |
| 2006/0136046 A1 | 6/2006 | Hartley et al. ............... 623/1.35 | | | |
| 2006/0136047 A1* | 6/2006 | Obermiller et al. ......... 623/1.41 | | | |
| 2006/0142846 A1 | 6/2006 | Pavcnik et al. .............. 623/1.24 | | | |
| 2006/0155363 A1 | 7/2006 | LaDuca et al. .............. 623/1.16 | | | |
| 2006/0155366 A1 | 7/2006 | LaDuca et al. .............. 623/1.23 | | | |
| 2006/0161248 A1 | 7/2006 | Case et al. ................... 623/2.1 | | | |
| 2006/0165753 A1 | 7/2006 | Richard ....................... 424/423 | | | |
| 2006/0171981 A1 | 8/2006 | Richard et al. .............. 424/422 | | | |
| 2006/0173532 A1 | 8/2006 | Flagle et al. ................ 623/1.24 | | | |
| 2006/0178729 A1 | 8/2006 | Thielen et al. | | | |
| 2006/0178730 A1 | 8/2006 | Hill et al. | | | |
| 2006/0195004 A1 | 8/2006 | Jarvik | | | |
| 2006/0206189 A1 | 9/2006 | Furst et al. ................... 623/1.11 | | | |
| 2006/0210597 A1 | 9/2006 | Hiles ........................... 424/422 | | | |

FOREIGN PATENT DOCUMENTS

| | | |
|---|---|---|
| JP | S62-27352 | 8/1994 |
| WO | 8302225 | 7/1983 |
| WO | 0154625 | 8/2001 |
| WO | 03030776 | 4/2003 |

OTHER PUBLICATIONS

U.S. Appl. No. 12/614,878, Final Office Action mailed on Dec. 27, 2010.

* cited by examiner

IMPLANTABLE DEVICE WITH REMODELABLE MATERIAL AND COVERING MATERIAL

RELATED APPLICATIONS

This application is a continuation-in-part of co-pending U.S. patent application Ser. No. 10/828,716, entitled "Artificial Valve Prosthesis with Improved Flow Dynamics," filed Aug. 30, 2004 by Case et al., which is incorporated herein by reference in its entirety; this application is also a continuation-in-part of co-pending U.S. patent application Ser. No. 11/056,903, entitled "Percutaneously Placed Prosthesis with Thromboresistant Valve Portion," filed Feb. 11, 2005 by Case et al., and claiming the benefit of U.S. provisional patent application 60/543,753, filed Feb. 11, 2004, both of which are incorporated herein by reference in their entirety; this application is also a continuation-in-part of co-pending U.S. patent application Ser. No. 10/642,372, entitled "Implantable Vascular Device," filed Aug. 15, 2003 by Pavcnik, Case et al., which is itself a continuation-in-part of U.S. patent application Ser. No. 09/777,091, filed on Feb. 5, 2001, and which also claims the benefit of U.S. provisional application 60/403,783, filed Aug. 15, 2002 and incorporated herein by reference in its entirety; this application is also a continuation-in-part of co-pending U.S. patent application Ser. No. 11/494,424, entitled "Implantable Thromboresistant Valve," filed Jul. 27, 2006 and incorporated by reference herein in its entirety; and this application also claims the benefit of U.S. provisional patent application 60/753,902, filed Dec. 23, 2005 and incorporated by reference herein in the entirety.

TECHNICAL FIELD

The present invention relates to medical devices for implantation in a body vessel. More particularly, the present invention relates to implantable medical device frames comprising a remodelable material.

BACKGROUND

Various implantable medical devices are advantageously inserted within various body vessels, for example to improve or replace the function of native valves therein. For example, native valves within the heart and veins function to regulate blood flow within the body. Heart valves positioned within the heart direct the flow of blood to and from other organs and pump oxygenated blood to the rest of the body. Venous valves are typically bicuspid valves positioned at varying intervals within veins to permit substantially unidirectional blood to flow toward the heart.

Minimally invasive techniques and instruments for placement of intraluminal medical devices have been developed to treat and repair undesirable conditions within body vessels, including treatment of conditions that affect blood flow such as venous valve insufficiency. Various percutaneous methods of implanting medical devices within the body using intraluminal transcatheter delivery systems can be used to treat a variety of conditions. One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Intraluminal medical devices can be deployed in a body vessel at a point of treatment and the delivery device subsequently withdrawn from the vessel, while the medical device retained within the vessel to provide sustained improvement in vascular valve function or to increase vessel patency.

Various types of medical devices are advantageously implanted within the body, such as within a blood vessel or within the heart, to treat a variety of conditions. One type of implantable medical device is an endovascular prosthesis that is used to strengthen a blood vessel wall in the location of an aneurysm, or to open an occlusion in a blood vessel. Another common type of medical device is a prosthetic valve. Valves have been implanted in and near the heart and at various positions within the venous system using catheter-based delivery techniques, including the implantation of prosthetic venous valves in the femoral and popliteal veins. Prosthetic valves can also be implanted in various body passages to replace natural valves that are defective or diseased. Prosthetic cardiac valves have been used to replace the native cardiac valves within the heart using percutaneous approaches. Prosthetic valves have also been implanted in veins to promote the flow of blood back to the heart. Blood pressure, as provided by heart activity via the arteries, is normally sufficient to maintain the flow of blood in one direction. The blood pressure in the veins can be much lower than in the arteries principally due to their distance from the heart. Venous valves function to limit the backflow of blood through the veins. Numerous such venous valves are located throughout the venous system and are particularly important to maintaining proper blood flow in the lower extremities. Venous valves can become incompetent and lead to chronic venous insufficiency. Various techniques have been developed for treating incompetent venous valves including valvuloplasty, transplantation, and replacement with a prosthetic valve. These techniques include both open and percutaneous approaches.

Inhibiting or preventing thrombosis and platelet deposition on an implantable device within the body is important in promoting continued function of the medical device within the body, particularly within blood vessels. Post-implantation thrombosis and platelet deposition on surfaces of implantable medical devices prosthesis undesirably reduce the patency rate of many implantable medical devices. For example, thrombosis and platelet deposition within an endovascular prosthesis may occlude the conduit defined by the endovascular prosthesis or compromise the function of an implanted valve by limiting the motion or responsiveness of moveable portions of the device such as valve leaflets. Many factors contribute to thrombosis and platelet deposition on the surfaces of implanted prosthesis. The properties of the material or materials forming the endovascular prosthesis are believed to be one important factor that can contribute to the likelihood of undesirable levels of post-implantation thrombus formation or platelet deposition on the implanted device. The formation of blood clots, or thrombus, on the surface of an endovascular prosthesis can both degrade the intended performance of the prosthesis and even undesirably restrict or occlude desirable fluid flow within a body vessel.

What is needed are implantable medical devices configured to mitigate or prevent thrombosis or promote the remodeling of portions of the device within a body vessel. The implantable medical devices provided herein are configured to provide implantable medical devices suitable for percutaneously delivery, such as venous valves or heart valves, that include a remodelable material and can be delivered using a minimally invasive catheter-based delivery system.

SUMMARY

Preferred embodiments of the invention relate to medical devices for implantation in a body vessel. The medical devices preferably include a covering material portion and a remodelable material portion, and preferably include a valve means for regulating fluid flow in a body vessel. Preferably, the remodelable material forms a portion of a valve means, for example a valve leaflet. Medical devices may be radially compressible, being configured for transcatheter percutaneous delivery in a body vessel, and radial expansion at a point of treatment within the body vessel.

The covering material portion preferably comprises a non-remodelable biostable material forming an outer surface of the medical device. For example, the covering material can be configured as a sleeve around the outside of a medical device, and can be positioned to contact the body vessel wall upon implantation of the medical device. The covering material can define an interior lumen of a tubular medical device.

The remodelable material is preferably positioned within the lumen defined by the covering material. Desirably, the remodelable material does not contact the body vessel wall upon implantation of the medical device in a body vessel. Upon implantation of the medical device, the covering material is preferably positioned between a body vessel wall and the remodelable material, for example to prevent or slow intimal tissue ingrowth from the body vessel wall into the remodelable material, or to mitigate or prevent thrombosis formation on the remodelable material.

Remodelable materials can permit rapid ingrowth of body tissue into the material and subsequent resorption upon implantation, for example by providing a matrix or support for the growth of new tissue thereon. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions of the medical device. Extracellular matrix materials, such as small intestine submucosa, are one exemplary type of remodelable material. One particularly preferred remodelable material is an extracellular matrix material, such as the materials disclosed in U.S. Pat. No. 6,206,931 to Cook et al., which is incorporated herein by reference in its entirety.

The medical device can further comprise a support frame attached to the covering material. The support frame can have any suitable configuration, but preferably provides a shape to a flexible covering material. The support frame can comprise a plurality of longitudinally-spaced ring structures attached to the covering at the distal end and proximal end. The ring structures can have a plurality of struts and bends to form an annular serpentine configuration. Radially self-expanding ring structures formed from materials such as a nickel-titanium alloy can provide an outward force against the vessel wall and may retain the covering material in a desired shape. The degree of radial force provided by a self-expanding ring structure can be increased by increasing the number of struts and bends in the ring, increasing the thickness of the struts or bends, and/or increasing the diameter of the ring structure relative to the size of the body vessel. The ring structures can provide rigidity and form to the covering, and are preferably attached to the outside surface of the covering. Preferably, the ring structures are formed from a radially expandable self-expanding material. The covering can be configured as a flexible outer sleeve attached to the support frame to form a cylindrical tubular device. Preferably, the covering material attached to the support frame is a non-remodelable material.

The medical device can be configured as an implantable valve comprising an outer covering material shaped as a sleeve defining an interior lumen and enclosing a valve means for regulating fluid flow through the interior lumen. The valve means can include one or more flexible valve leaflets positioned within the interior lumen, and moveable between an open and closed position in response to fluid flow within the interior lumen. The valve means can further include a valve support frame, to which the one or more valve leaflets can be attached. The valve support frame can have any suitable configuration, and is preferably attached to the covering material. Preferably, one or more valve leaflets adapted to regulate the flow of fluid through the interior lumen of the medical device are formed from the remodelable material attached to a valve support frame. The valve support frame is preferably attached to a tubular covering positioned around the valve support frame and extending longitudinally from one or both ends of the valve support frame.

The medical devices can be radially expanded from a compressed delivery configuration to an expanded deployment configuration. Medical devices can be delivered intraluminally, for example using various types of delivery catheters, and expanded by conventional methods such as balloon expansion or self-expansion. In one embodiment, the medical device can be an implantable radially expandable medical device moveable from a radially compressed state to a radially expanded state, and having an interior surface defining an interior lumen and an exterior surface. The medical device can include a substantially non-remodelable covering material configured as a tubular sleeve having an abluminal side defining at least a portion of the exterior surface of the medical device and a luminal side; and a remodelable material positioned within the portion of the interior lumen defined by the covering material. Optionally, a valve means comprising a valve leaflet formed in part from the remodelable material can be positioned at least partially within the interior lumen of the medical device.

Other embodiments provide methods of making medical devices described herein, such as methods of attaching the covering material to the frame. One method of manufacturing a radially expandable medical device can include the steps of providing a radially expandable valve comprising a valve support frame and at least one valve leaflet comprising a remodelable material attached to the valve support frame, attaching a covering material configured as a tube comprising a non-remodelable material to the valve support frame so as to enclose the at least one valve leaflet, the covering material having an exterior surface and an interior surface; and attaching a support frame comprising a plurality of ring support structures to the covering material. Still other embodiments provide methods of treating a subject, which can be animal or human, comprising the step of implanting one or more medical devices as described herein.

Methods for delivering a medical device as described herein to any suitable body vessel are also provided, such as a vein, artery, biliary duct, ureteral vessel, body passage or portion of the alimentary canal. In some embodiments, medical devices having a frame with a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, subclavian, aorta, intracranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the medical device.

Additional understanding of the invention can be obtained by with respect to certain preferred embodiments of the invention described herein.

DETAILED DESCRIPTION

Figure 1A:
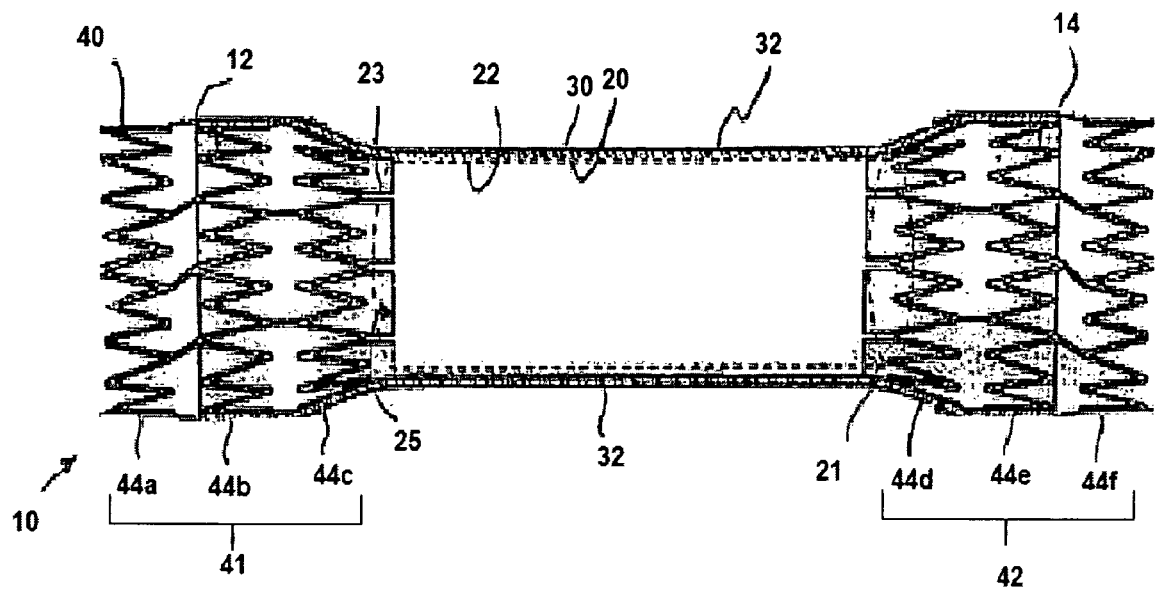
FIG. 1A is a side view of a first medical device embodiment configured as a stent graft comprising an outer covering enclosing a remodelable material.

The following detailed description and appended drawings describe and illustrate various exemplary embodiments of the invention.

Definitions

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or implantation of foreign objects into a living organism.

A large number of different types of materials are known in the art which may be inserted within the body and later dissipate. The term "bioabsorbable" is used herein to refer to materials selected to dissipate upon implantation within a body, independent of which mechanisms by which dissipation can occur, such as dissolution, degradation, absorption and excretion. The terms "bioabsorbable," "resorbable" or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, bioabsorbable, and biodegradable, without implying the exclusion of the other classes of materials.

"Non-bioabsorbable" material refers to a material, such as a polymer or copolymer, which remains in the body without substantial bioabsorption.

The terms "remodelable" or "bioremodelable" as used herein refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about 5 days to about 6 months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately.

The term "non-remodelable" refers to a material that is not a remodelable material, that is, a material that is not selected or configured to promote or induce tissue growth upon contacting living tissue. A non-remodelable material preferably does not contain biological molecules (such as growth factors) that promote tissue ingrowth, angiogenesis, and other growth processes within the material. Non-remodelable materials include biostable or bioabsorbable polymers, as well as forms of collagen or other biomolecules configured or treated to slow tissue ingrowth. For example, a cross-linked extracellular matrix material configured and treated to substantially retard or prevent tissue ingrowth can also be used as a non-remodelable material. Non-remodelable materials can be used as covering materials enclosing a remodelable material. Preferably, non-remodelable materials remain substantially intact within a body vessel for a period of time required for substantial ingrowth of new tissue in the enclosed remodelable material, typically on the order of between about 2 weeks to about 3 months.

As used herein, "substantially non-remodelable" materials include both non-remodelable materials and materials that permit limited tissue ingrowth at a much slower rate than the rate of tissue growth in the enclosed remodelable material. Tissue growth through the non-remodelable material is typically only observable after sufficient periods of implantation in a body vessel that permit substantial amounts of tissue growth in an enclosed remodelable material.

As used herein, the term "body vessel" means any body passage lumen that conducts fluid, including but not limited to blood vessels, esophageal, intestinal, billiary, urethral and ureteral passages.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The medical devices of the embodiments described herein may be oriented in any suitable absolute orientation with respect to a body vessel. The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

The terms "frame" and "support frame" are used interchangeably herein to refer to a structure that can be implanted, or adapted for implantation, within the lumen of a body vessel. As used herein, a "support frame" is any structure that is attached to the covering material, for example to hold the covering material in place within a body vessel, including an interior portion of a blood vessel, lymph vessel, ureter, bile duct or portion of the alimentary canal. A "valve support frame," as used herein, refers to a support frame that forms a portion of a valve means for modifying fluid flow within a body vessel. The valve support frame can have any suitable configuration, but is preferably a radially expandable structure comprising a plurality of struts and bends and enclosing an interior lumen. Preferably, one or more valve leaflets can be attached to the valve support frame.

The term "covering material" as used herein refers to a biostable or bioabsorbable material that is substantially non-remodelable. Preferably, the covering material is flexible and biocompatible. A covering material can have any suitable shape, but is preferably formed as a tubular covering on the outside of an implantable medical device. A covering material can be formed from any suitable material, but is preferably a suitably flexible, non-irritating, biocompatible and biostable polymer.

Medical Device Configurations

The invention relates to medical devices that include a covering material and a remodelable material. The medical device can be a percutaneously-deliverable, radially-expandable device having any suitable configuration, but is preferably a stent graft or a valve. The covering material is preferably a non-remodelable material placed between the remodelable material and the wall of a body vessel upon implantation of the medical device.

The medical device can optionally further comprise a support frame attached to the covering. The support frame can have any suitable configuration, but preferably provides a shape to a flexible covering material. The support frame can comprise a plurality of longitudinally displaced ring structures attached to the covering at the distal end and/or proximal end. The ring structures can have a plurality of struts and bends to form an annular serpentine configuration. The ring structures can provide rigidity and form to the covering, and are preferably attached to the outside surface of the covering. Preferably, the ring structures are formed from a radially expandable self-expanding material. The covering can be configured as a flexible outer sleeve attached to the support frame to form a cylindrical tubular device. Preferably, the covering material attached to the support frame is a non-remodelable material. In one aspect, the support frame comprises one or more radially expandable resilient sinusoidal ring structures attached to the outside of the covering. One or more ring structures can be longitudinally positioned around a valve structure contained within a tubular covering material sleeve and/or at the proximal or distal ends of the covering sleeve. Optionally, the covering material may contain a valve structure within a lumen, and may extend longitudinally in either direction from the valve structure. One or more ring structures may be attached to portions of the covering material extending longitudinally past the valve structure contained within a portion of the covering material lumen.

The medical device can include an intraluminally implantable frame defining a substantially cylindrical interior lumen. The frame can function as a support frame for an attached covering material. In one embodiment, the covering material is positioned on the exterior (abluminal) side of the medical device.

In a first embodiment, the medical device is configured as a stent graft. Referring to FIG. 1A, a medical device 10 is shown comprising a covering material 30, a remodelable material 20 and a support frame 40. The covering material 30 is configured as a first tube extending from a flared proximal end 12 to a flared distal end 14 and forming a portion of the exterior surface 32 of the medical device 10. The flared ends 12,14 have a larger diameter than the rest of the tubular covering material 30. A remodelable material 20 configured as a second tube is concentrically nested within the covering material 30, and extends from a remodelable material proximal end 23 to a remodelable material distal end 21. The remodelable material 20 (second tube) has a smaller diameter than, and is secured to, the covering material 30 (first tube), for example by sutures extending through both materials or by an adhesive between the two materials. The inner surface 22 of the remodelable material 20 defines a portion of a substantially cylindrical interior lumen 25 of the medical device. The remodelable material 20 and the covering material 30 can be selected to provide a desired amount of flexibility or rigidity to the medical device. Upon implantation within a body vessel, the exterior surface 32 of the medical device 10 can contact the wall of the body vessel, permitting blood to flow through the lumen 25 in any desired direction. The covering material 30 and the remodelable material 20 can have any suitable thickness, but are preferably between about 5 and about 200 microns thick.

The medical device also includes a support frame 40 formed from a plurality of sinusoidal rings formed from a material having sufficient rigidity to provide a desired tubular shape and sufficient resilience to prevent damage to a body vessel upon implantation. The support frame 40 includes a proximal portion 41 and a distal portion 42. The support frame 40 is formed from a plurality of sinusoidal ring members 44a-44f (together, 44) attached by a plurality of longitudinally-oriented struts between adjacent ring members 44. The support frame 40 can be formed from a self-expanding material such as a nickel titanium alloy selected to provide outward radial pressure against a body vessel so as to prevent movement of the medical device within the body vessel upon implantation therein. Both portions 41, 42 of the support frame 40 are attached to both the covering material 30 and the remodelable material 20 in medical device 10. Alternatively, the ring members 44 may be attached only to the covering material 30, without being attached to each other.

In other embodiments, the support frame can include additional ring members 44 between the proximal portion 41 and the distal portion 42. Ring members 44b, 44c, 44d and 44f preferably contact the internal surface of the covering material 30, and ring members 44c and 44d are attached to the distal end 23 and the proximal end 21 of the remodelable material 20. Additional ring members 44 may be positioned between the proximal end 23 and distal end 21 of the remodelable material. Optionally, ring members 44 may be positioned between the covering material 30 and the remodelable material 20, although the ring members 44 are preferably positioned outside the covering material 30.

Optionally, the support frame 40 can include longitudinal connecting members connecting the proximal portion 41 and the distal frame portion 42. Two or more longitudinal struts may extend between ring member 44d and ring member 44c, from the proximal end 23 to the distal end 21 of the remodelable material 20. The longitudinal struts are preferably positioned between the remodelable material 20 and the covering material 30, or outside the covering material. In medical device 10, ring members 44a and 44f are attached to ring members 44b and 44e, respectively, but are not attached to either the covering material 30 or the remodelable material 20. Alternatively, the ring members 44 can be positioned in any suitable configuration, including around the outside of the covering material 30, between the covering material 30 and the remodelable material 20, or inside the remodelable material 20. In other embodiments, the support structure does not include a support frame 40, or the support frame 40 does not include sinusoidal ring members 44. The medical device 10 can be used, for example, as a stent graft within a damaged blood vessel such as at the site of an aneurysm. In one embodiment, the medical device is configured as a vascular stent for implantation within body vessel, such as an infrapopliteal artery. In another embodiment, the medical device is configured for implantation in a hemodialysis fistula.

In a second embodiment, the medical device is configured as an implantable valve positioned within a lumen defined by a surrounding covering material. Preferred valve configurations include a covering material positioned between a valve means and the outer surface of the medical device. Certain non-limiting examples of valve configurations are provided herein to illustrate selected features of the medical devices. Medical devices can comprise one or more of the valve embodiments discussed below, or combinations, variations or portions thereof, as well as other valve configurations. Medical devices comprising various frames in combination with material suitable to form a leaflet attached thereto are also within the scope of some embodiments of the invention.

Figure 1B:
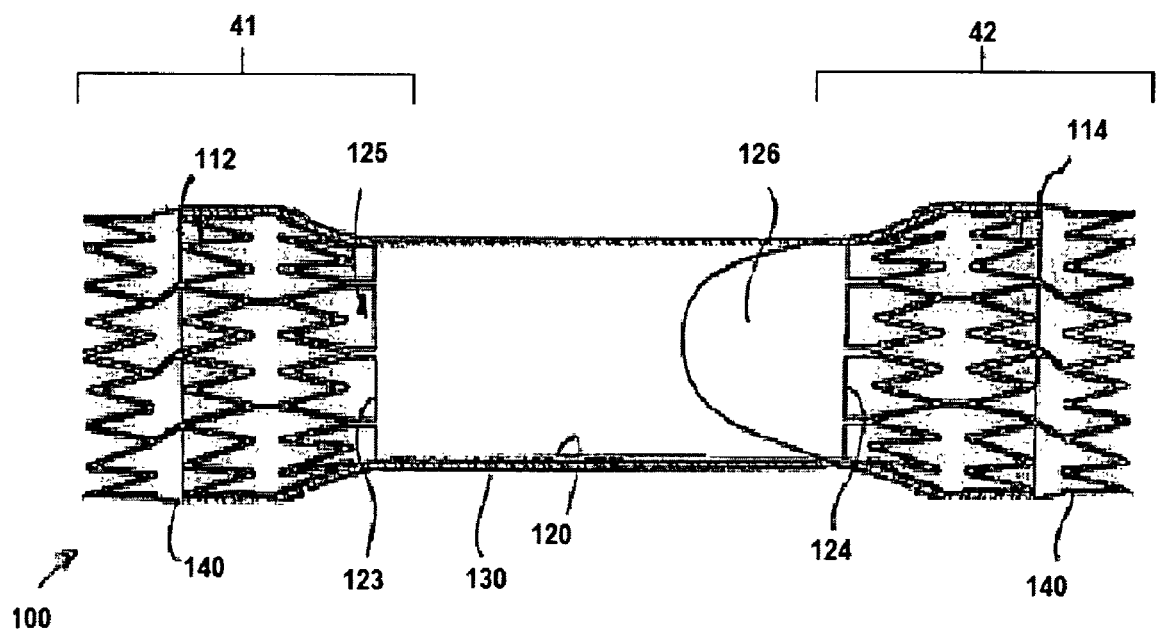
FIG. 1B is a side view of a second medical device embodiment configured as an implantable valve comprising an outer covering enclosing a frameless valve structure with two valve leaflet surfaces.

FIG. 1B shows a second medical device 100 comprising a covering material 130 enclosing a remodelable material 120, and a support frame 140 attached to the covering material 130. The second medical device 100 is configured as a valve.

The covering material 130 is configured as a tube flared at the proximal end 112 and the distal end 114. The frame 140 is the same as the frame 40 described in the first medical device 10, except as described herein, and includes a plurality of sinusoidal ring members forming a proximal and distal frame portion. The remodelable material 120 is nested inside a portion of the covering material 130, extends from a proximal end 123 to a distal end 124, and forms a valve means. The valve means is configured as a tube having a tapered portion 126. The distal end 124 of the remodelable material 120 is a flattened tube with two opposable edges defining a valve orifice. The distal end 124 of the remodelable material is not attached to the frame 140. The tapered portion 126 of the remodelable material 120 is flexible in response to fluid flowing through the lumen 125 of the medical device 100, permitting fluid to flow from the proximal end 112 toward the distal end 114 of the covering material and substantially preventing retrograde fluid flow in the opposite direction by closure of the valve orifice. Preferably, the medical device 100 is intended for use in a blood vessel having antegrade fluid flow proceeding in the direction toward the distal end 114. For example, for a vein, antegrade blood flow is in the direction toward the heart. Alternatively, the medical device may include a support frame and a covering materials attached to the interior (luminal) side of the support frame. The covering material 130 is preferably configured as a sleeve or ring of material. Optionally, the medical device can include multiple covering materials attached to a support frame.

The medical devices of some embodiments can be expandable from a compressed delivery configuration to an expanded deployment configuration. Medical devices can be delivered intraluminally, for example using various types of delivery catheters, and be expanded by conventional methods such as balloon expansion or self-expansion. Examples of balloon expandable frame materials include stainless steel and cobalt chromium alloys. Optionally, bioactive materials and/or polymer coatings can be adhered on a balloon expandable metal structure such as those formed from stainless steel or cobalt-chromium. Alternatively, the frame material can be a self-expanding material such as the nickel-titanium alloy Nitinol.

Figure 2A:
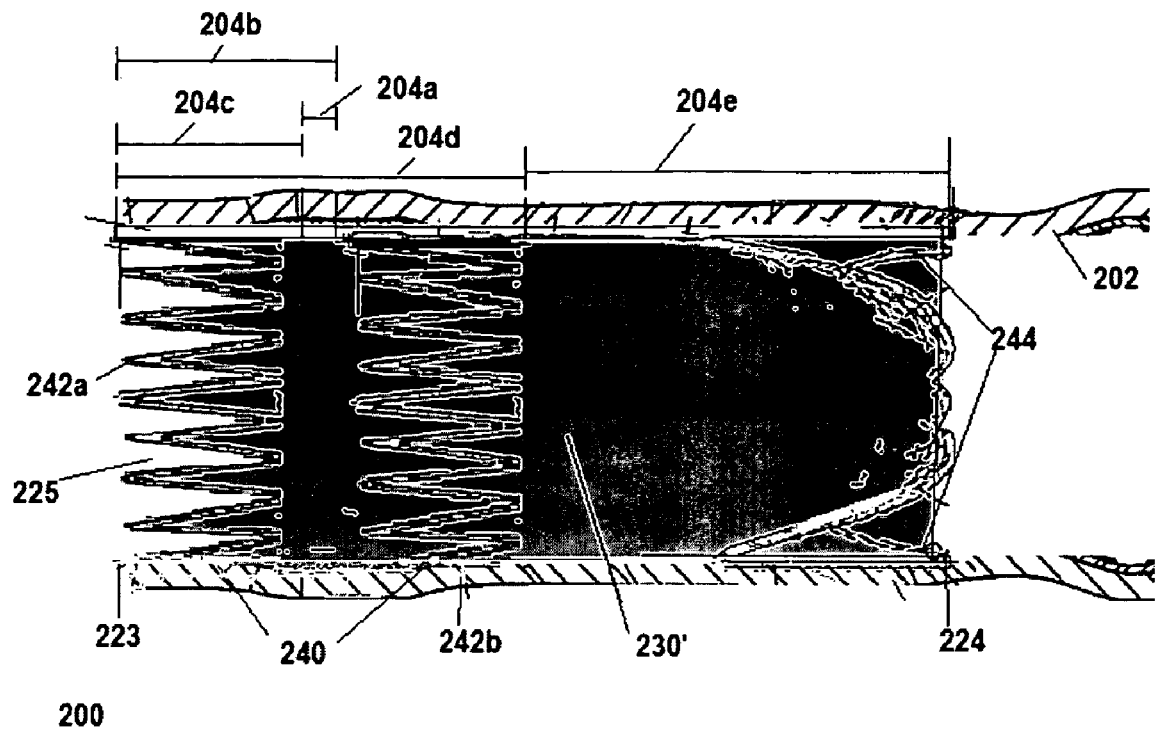
FIG. 2A is a top view of a third medical device embodiment congfigured as an implantable valve comprising an outer covering enclosing a first valve structure and positioned within a portion of a body vessel.
Figure 2B:
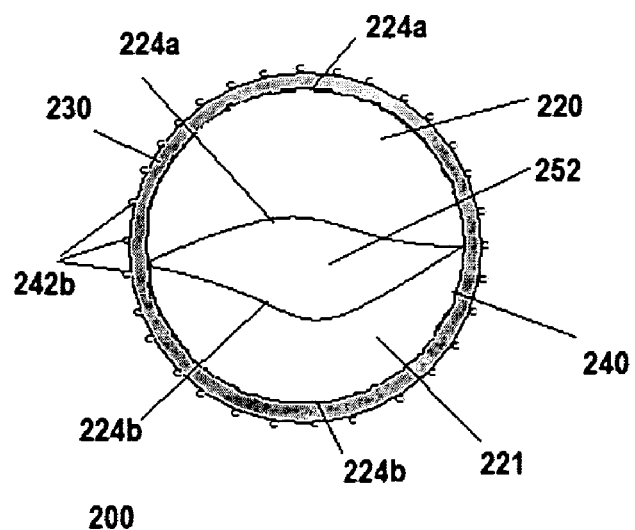
FIG. 2B is an end view of the third medical device embodiment shown in FIGS. 2A within the portion of the body vessel.
Figure 2C:
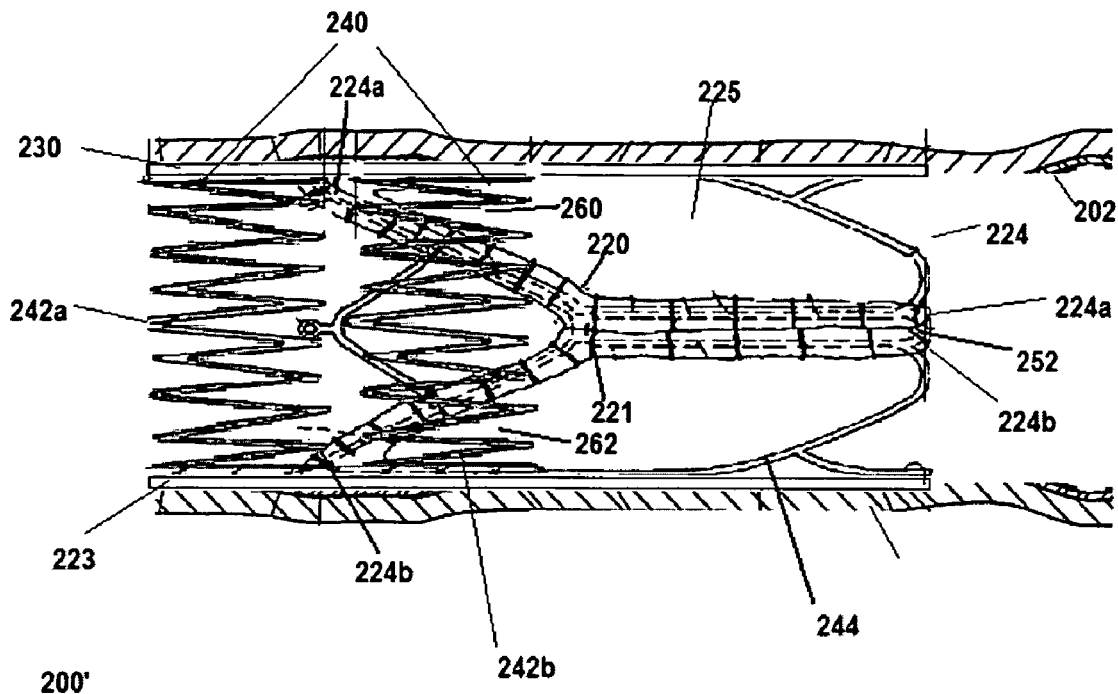
FIG. 2C is a top view of the third medical device embodiment shown in FIG. 2A within the portion of the body vessel, with a transparent covering sleeve portion showing the first valve structure comprising a first support frame and a pair of opposable valve leaflets positioned within the lumen of the covering sleeve.
Figure 2D:
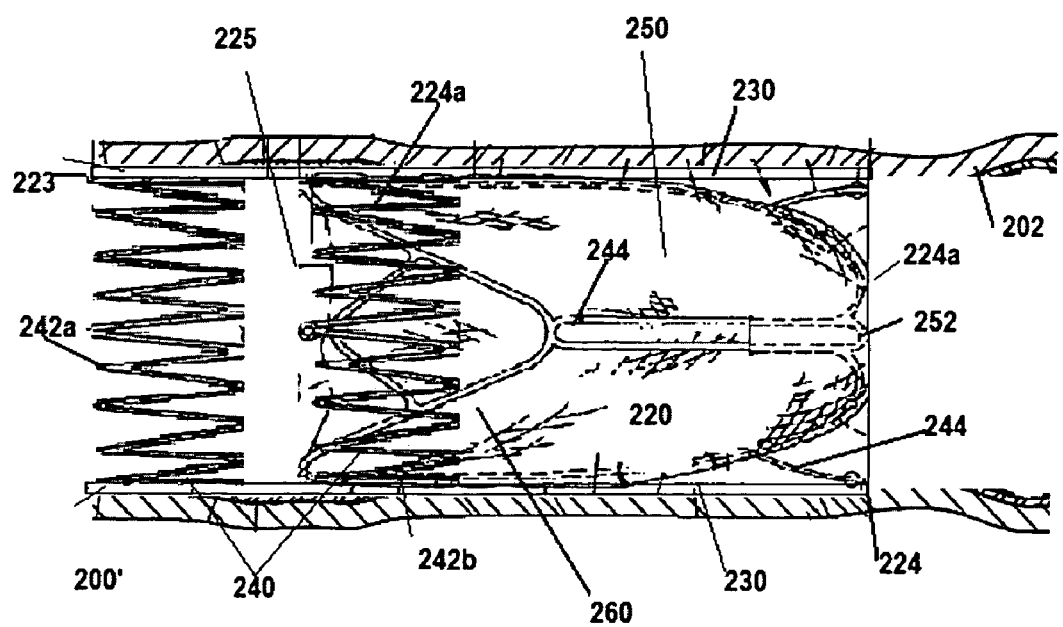
FIG. 2D is a side view of the third medical device embodiment shown in FIG. 2C within the portion of the body vessel.

FIGS. 2A-2D illustrate a third medical device 200 comprising a support frame 240, a pair of opposable valve leaflets 220, 221 formed from a remodelable material, and a covering material 230. FIG. 2A is a side view of the medical device 200 within a body vessel segment 202 with an opaque covering material 230'; FIG. 2B shows an end view of the distal end of the medical device shown in FIG. 2A; FIG. 2C is a side view of the medical device 200' with a transparent covering material 230; FIG. 2D is a rotated side view of the medical device 200' shown in FIG. 2C.

The support frame 240 comprises two sinusoidal ring members 242a, 242b (together, 242) positioned around the outside of the covering material 230. The covering material 230 is attached to each ring member 242 by any suitable attachment means. The covering material 230 is configured as a tubular sleeve extending from a proximal end 223 to a distal end 224 and defining a cylindrical interior lumen 225. The covering material 230 may be attached to each ring member 242 by a plurality of sutures (e.g., 6-0 monofilament polypropylene sutures) passing through the covering material 230 and around a portion of the ring member 242. While the medical devices 200, 200' include two ring members 242, other embodiments may include any suitable number of ring members 242, including alternative embodiments with 1, 3, 4, 5, 6, 7, 8, 9, 10 or more ring members positioned coaxially along the longitudinal axis of the covering material 230.

Preferably, at least one ring member 242 is positioned at the proximal end 223 of the medical device 200, 200' and/or the distal end 224 of the medical device 200, 200'. In the medical devices 200, 200', the ring members 242 in medical device 200 are not attached to each other, but are secured to the medical device 200 by suture attachment to the outside of the covering material 230. Each ring member 242 is radially self-expanding and sized to provide a radially outward force to the covering material 230 at the attachment points between the covering material 230 and the ring members 242. Longitudinally adjacent ring members 242 may be positioned at any suitable longitudinal distance 204a from each other. The distance 204a is preferably sufficient to provide a desired flexibility and to maintain a desired shape to the covering material 230. For example, for ring members 242 having an outer diameter of about 10-15 mm, the distance 204a may be about 3-5 mm. Other distances 204b, 204c, 204d, 204e are indicated in FIG. 2A may be varied to provide a medical device with appropriate flexibility and shape for an intended use. Preferably, the ring members 242 are configured to provide a desired shape to the covering material 230. Self-expanding ring members 242 can be used to retain the covering material 230 at a desired distance from a remodelable material attached to a second frame within the lumen defined by the covering material 230. Alternatively, the ring members 242 may be connected by one or more longitudinal struts, woven materials or other structures.

A valve 250 is positioned within the covering material 230. The valve 250 is formed from a second frame 244 attached to a first valve leaflet 220 and a second valve leaflet 221. The valve leaflets 220, 221 are formed from a remodelable material such as small intestine submucosa (SIS) and are sewn onto the frame to form two separate leaflets. The distal end 224a of the first valve leaflet 220 and the distal end 224b of the second valve leaflet 221 form opposable flexible free edges that move relative to one another in response to fluid flow, defining a valve orifice 252. The valve orifice 252 opens to permit fluid flowing from the proximal to the distal end of the medical device lumen, while closing to substantially prevent retrograde fluid flow in the opposite direction. The distal end 224a of the first valve leaflet 220 and the distal end 224b of the second valve leaflet 221 contacts the inner surface of the covering material 230, and can be attached thereto. Retrograde fluid flow can collect in a sinus region 260, 262 between the covering material 230 and the surface of each valve leaflet 220, 221 (respectively) facing the covering material 230. When the valve orifice 252 re-opens in response to fluid flow, the fluid collected in the sinus region 260, 262 can be expelled in the direction of fluid flow.

The ring members 242 are positioned to provide desirable fluid flow properties around the valve 250. Preferably a first self-expandable ring member 242a providing a desired force in an outward radial direction is positioned near the proximate end of the valve 250 to maintain a lumen defined by the covering material 230 that provides a desired rate of fluid flow into the valve 250. In addition, a second ring member 242b is positioned around a portion of the valve 250, distal to the first ring member 242a. The second ring member 242b is preferably positioned around the base of the valve leaflets 220, 221, to radially expand the covering material to prevent pooling of fluid in the sinus regions 260, 262. The second frame 244 may also be a self-expanding frame that exerts radial force outward against the interior (luminal) surface of the covering material 230 and toward the wall of the body vessel 202.

Figure 3A:
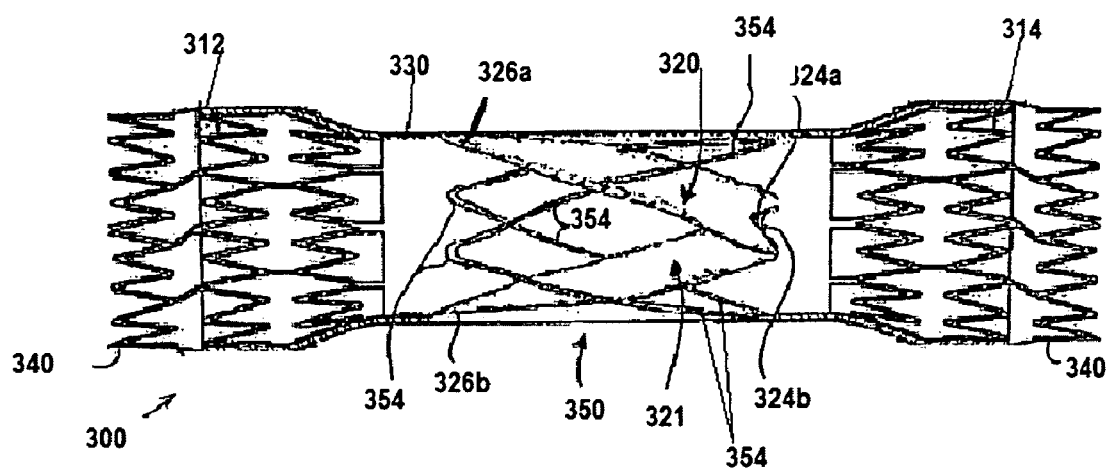
FIG. 3A is a side view of a fourth medical device embodiment configured as an implantable valve comprising a transparent outer covering sleeve with a second valve structure positioned within the lumen of the covering sleeve, the second valve structure including a pair of opposable flexible valve leaflets attached to a second support frame structure.

FIG. 3A shows another medical device 300 comprising a frame 340, a covering material 330 configured as a tube extending from a proximal end 312 to a distal end 314, and a valve 350 positioned within the covering material 330. The medical device 300 is substantially similar to the medical device 100, except as described herein. The valve 350 includes a first valve leaflet 320 and a second valve leaflet 321 attached to a valve support frame 354. The valve support frame 354 can be attached to the covering material 330. The first valve leaflet 320 and the second valve leaflet 321 are sewn to the valve support frame 354 and extend from a proximal end 326a, 326 b (respectively) to a distal free edge 324a, 324b (respectively). The distal free edges 324a, 324b form a valve orifice permitting fluid flow in substantially one direction, from the proximal end 312 of the covering material toward the distal end 314 of the covering material. The first leaflet free edge 324a is positioned in apposition to the second leaflet free edge 324b to define the valve orifice.

The valve leaflets 320, 321 can have any suitable shape. Preferably, the valve leaflet includes one or more edges attached to a valve support frame 354 placed within the lumen defined by the covering material 330. The valve leaflet 320, 321 can have (n) edges and (n–1) edges of each valve leaflet preferably contact the covering material 330 to form a sinus region between the valve leaflet and the covering material; where (n) is an integer equal to 2 or greater. Valve leaflets with (n) of 2, 3, or 4 are preferred, although leaflets with other shapes can also be used. Preferably, at least 2 edges of a valve leaflet are attached to a valve support frame, and at least one edge of a valve leaflet is a leaflet free edge that is not attached to any support frame. Referring again to FIG. 3A, separate sinus regions are formed between the surface of the first leaflet 320 and the interior surface of the covering material 330, and between the second leaflet 321 and the opposite interior surface of the covering material 330. Each leaflet 320, 321 has three edges, one of which is the free edge 324a, 324b. The remaining two edges are attached to the valve support frame 354.

Figure 3B:
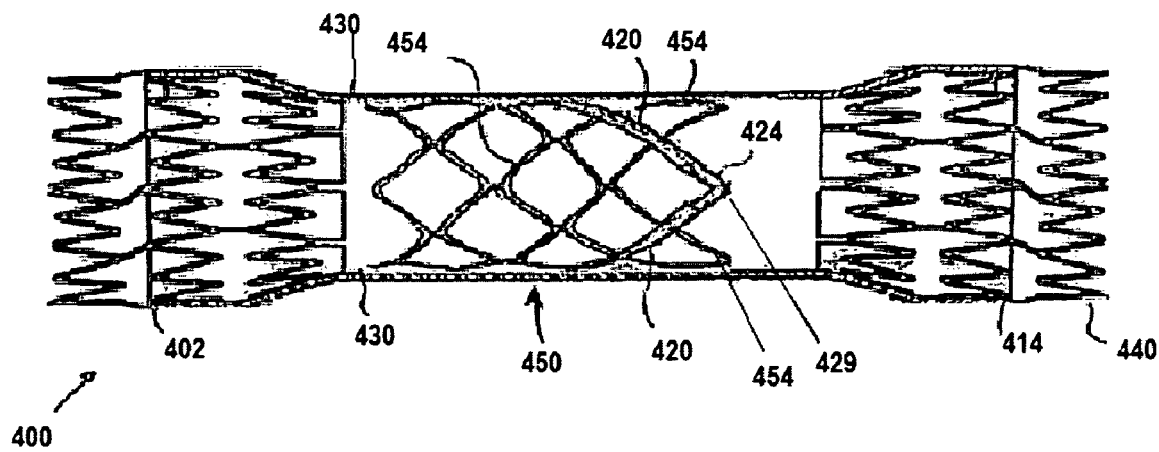
FIG. 3B is a side view of a fifth medical device embodiment configured as an implantable valve comprising a transparent outer covering sleeve with a third valve structure positioned within the lumen of the covering sleeve, the third valve structure including a pair of opposable flexible valve leaflets attached to a third support frame structure.

FIG. 3B shows another medical device 400 comprising a frame 440, a covering material 430 configured as a tube, and a valve 450 positioned within the covering material 430. The medical device 400 is substantially similar to the medical device 300, except as described herein. The valve 450 includes a pair of valve leaflets 420 attached to a tubular valve support frame 454. The valve support frame 454 can be attached to the covering material 430. The valve leaflets 420 are sewn to the valve support frame 454 and include a pair of opposable free edges 424. The free edges 424 form a valve orifice 429 permitting fluid flow in substantially one direction through the covering material 430.

While the valves illustrated herein each include two valve leaflets, valves with any suitable number of leaflets are also provided. Valves with 2 or 3 valve leaflets are particularly preferred, although valves with 1, 4, 5, 6 or more valve leaflets are also provided herein. Preferably, each valve leaflet includes at least one leaflet free edge that is not attached to a support frame. More preferably, each valve defines a moveable valve orifice defined by one or more valve leaflet free edges. Most preferably, a valve orifice is defined by two or more valve leaflet free edges positioned in apposition to one another.

Figure 4:
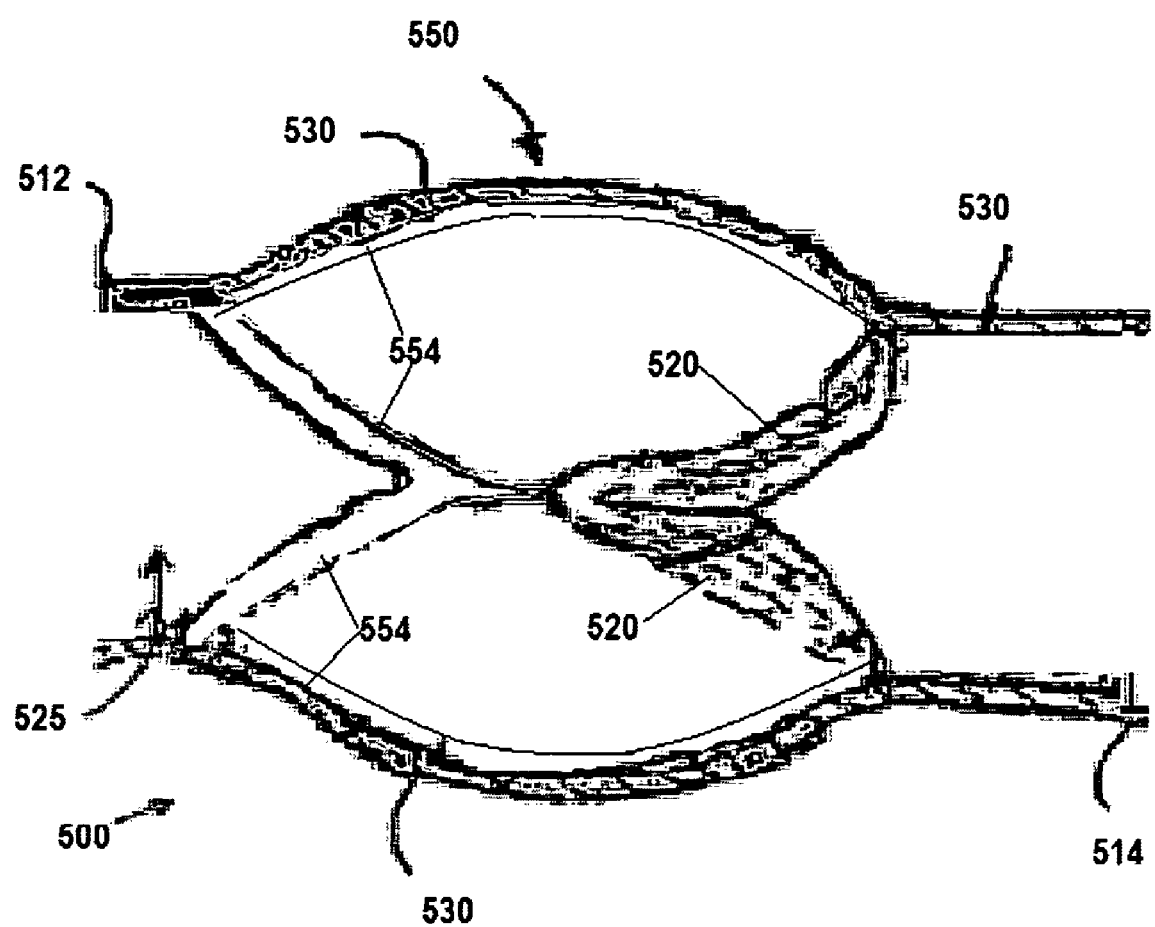
FIG. 4 shows a sixth medical device embodiment configured as an implantable valve comprising a covering material having a bulbous configuration, and a fourth valve structure positioned within the lumen of the covering material.

FIG. 4 shows another medical device 500 comprising an outer covering 530 positioned around a valve 550. The medical device 500 is supported by a valve support frame 554 comprising a plurality of arcuate molded members forming a bulbous spherical shape having a plurality of openings, but does not include any sinusoidal ring structures. The outer covering 530 is a covering material extending from a proximal end 512 to a distal end 514 of the medical device 500, around the outside of the valve support frame 554. The valve 550 includes a pair of valve leaflets 520 attached to the valve support frame 554, and positioned between the covering material 530 and the interior lumen 525 of the medical device 500. The valve support frame 554 defines a bulbous sinus shaped sinus surrounding the valve leaflets 520. Unlike certain device embodiments above, the valve leaflets 520 are positioned to permit fluid flow from the distal end 514 toward the proximal end 512.

Figure 5:
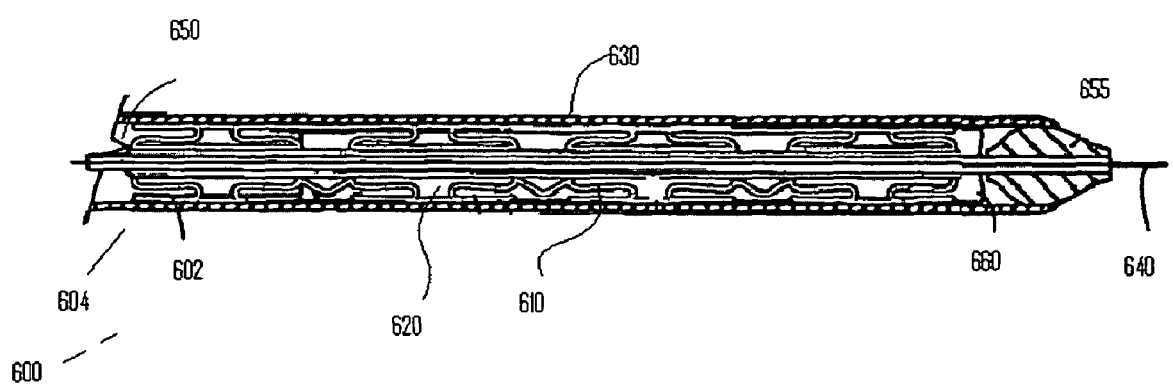
FIG. 5 shows a cross sectional view of an implantable medical device in the compressed state in a delivery catheter.

FIG. 5 shows a medical device 602 in a radially compressed configuration 600 within the distal end of a delivery catheter 650. The medical device 602 can be any medical device, including medical devices 10, 100, 200, 200', 300, 400 or 500 described above, having an outer covering material 630 enclosing a remodelable material 620 within the covering material 630. The medical device 602 is preferably configured as a stent graft or valve, and typically includes one or more support frames 610.

The medical device 602 is radially expandable from a low profile, radially compressed configuration to an expanded configuration by balloon expansion or self-expansion. The embodiment illustrated in FIG. 5 shows a balloon expandable medical device 602. The delivery catheter 650 includes a balloon 660 that is annularly enclosed by the medical device 602 and is inflatable to radially expand the medical device 602 by outward pressure. Alternatively, the medical device 602 can include a self-expanding ring member and the delivery catheter 650 can be provided without the balloon. Instead, a delivery catheter 650 for a self-expanding medical device may include a retractable means for restraining the medical device in a radially compressed state. The means for restraining the medical device can be retracted to permit the medical device to expand to a radially expanded configuration. Typically, a self-expanding medical device can have a smaller outer diameter in the radially compressed state than a balloon expandable medical device. Delivery catheters 650 for balloon expandable medical devices typically have an outer diameter of about 12-15 french, while the diameter of delivery catheters for self-expanding medical devices are typically about 10-12 french. The medical device 602 extends from the proximal end 604 to the distal end 660 of the catheter 650.

The delivery catheter 650 is fitted over a guidewire 640 for delivery to a blood vessel such as an artery or vein by conventional percutaneous transluminal methods. The distal portion 655 of the delivery catheter 650 can be placed within a body vessel at a desired point of treatment, and the balloon 660 can be inflated. The medical device 602 may be deployed by radial expansion of the balloon 660 within a body vessel. The catheter 650 is positioned at a point of treatment within a body vessel. The balloon 660 is then inflated to expand the medical device 602 to the radially expanded configuration. Upon inflation of the balloon, the covering material 630 contacts the interior surface of the body vessel. Subsequently, the balloon 660 can be deflated and the delivery catheter 650 removed from the body vessel along the guidewire 640.

Alternatively, the support frame 610 can comprise a self-expanding material such as nitinol. A medical device 602 comprising a self-expanding support frame 610 can be deployed from a catheter that includes a moveable sheath containing the support frame instead of a balloon. The sheath can be longitudinally translated with respect to the medical device, away from the distal end of the delivery catheter. When the sheath no longer covers the medical device, the self-expanding support frame can radially expand to contact the inner wall of the body vessel, where the medical device can be maintained by the outward force exerted by the frame or by barbs or perforations in the exterior surface of the medical device. The delivery catheter 650 for delivery of a self-expanding medical device may be positioned in a body vessel and the retractable means for restraining the medical device can be retracted to permit radial expansion of the medical device until the covering material 630 contacts the wall of the body vessel.

The frame can also comprise a means for orienting the frame within a body lumen, such as a radiopaque region. For example, the frame can comprise a marker, or a delivery device comprising the frame can provide indicia relating to the orientation of the frame within the body vessel. The marker can be a radiopaque portion of the frame detectable by imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Radiopaque, physiologically compatible materials include metals and alloys selected from the transition metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. Highly preferred is a platinum/tungsten alloy, e.g., 8% tungsten and the remainder platinum. The particular form and choice of material used for the implantable frame will depend on the desired application. Preferably, a radiopaque material such as gold may be mechanically compressed to form an isolated region, such as a small circular "button" or "eyelet," that can be identified by remote imaging techniques, such as X-ray imaging.

Covering Material

The covering can be formed from any suitable non-remodelable biocompatible materials, including bioabsorbable or biostable polymers. The covering material is preferably made from a non-remodelable biostable material that is biocompatible and provides physical properties commensurate with an intended therapeutic use. For example, the thickness, dimensions, water permeability, and material selected for the covering material are preferably selected for a desired application.

The size, shape, and thickness of the covering material are preferably selected to permit a desired degree of radial compression of the medical device to achieve a desired radius for implantation from a catheter. Typically, a medical device may comprise a covering with a thickness permitting radial compression of the device to a size suitable for delivery from a delivery catheter having a 10-15-french, or preferably about 12-french, outer diameter. The thickness of the covering material is preferably less than about 0.012-inch (0.30 mm), more preferably less than about 0.008-inch (0.20 mm), and most preferably about 0.002-inch to about 0.005-inch (about 0.051 to 0.127 mm). The covering material thickness may also be chosen to provide adequate strength, rigidity and/or flexibility to the material. Typically, medical devices comprising self-expanding frames may be configured for use with a delivery catheter having a smaller diameter (e.g., about 10-french) than balloon-expandable frames, which may fit into a delivery catheter device with a diameter of about 12-french.

The covering material thickness is preferably chosen to permit the covering material to withstand pulsatile hemodynamic pressure and torsion of a body vessel upon implantation in a body vessel, without damaging the covering material or causing migration of the covering material from a position between the vessel wall and the remodelable material. In a tubular configuration, the circumferential tensile strength of the covering material is preferably at least about 5 N/mm, more preferably at least about 7 N/mm or greater, including 5, 6, 7, 8, 9, 10, 11, 12, 13, 14 or 15 N/mm; the longitudinal tensile strength of the covering material in the tubular configuration is preferably at least about 40 N/m, more preferably about 44 N/mm or greater, including 40, 41, 42, 43, 44, 45, 46, 47, 48, 49, or 50 N/mm. The covering material may be prepared as a laminar sheet that is rolled into a tube with opposable ends of the sheet joined together to form the tubular sheet. The ends of the sheet may be sewn together using a suitable suture, such as a 5.0 polyvinyl braided suture. The covering material may also be manufactured as a tube having one or more layers, for example by weaving. In one aspect, a covering material tube can be woven around a tube of remodelable material to form a two-layer structure. For example, a two-layer tube may include an inner remodelable surface formed from an extracellular matrix material and an outer non-remodelable material formed from a PET covering material.

The covering portion of a medical device may be made from a textile, polymer, or other suitable non-remodelable material with a desired strength and durability. The covering material may also be selected to provide a desired level of water permeability. Preferably, the water permeability of the covering material is selected to provide a desired level of liquid communication between the vessel wall and the remodelable material. Optionally, a moisture barrier material may be used as a covering material to reduce or prevent communication of liquid from the vessel wall from contacting the remodelable material. The remodelable material may contact fluid passing through the lumen of the medical device with greater incidence than fluid passing around the outside of the medical device, on the outside of the moisture barrier. The water permeability of the covering portion may also be selected to reduce fluid interaction between the vessel wall and the remodelable material, for example to reduce or prevent thrombotic events proximate the valve portion of the device. Preferably, the covering material has a low water permeability that is less than about 1,500 ml/min/cm$^2$ and more preferably less than about 1,200, 1,000, 500, 250, 100, 75, or 50 ml/min/cm$^2$, and most preferably less than 25 ml/min/cm$^2$. For example, Schurmann et al. describe a study of stent-grafts formed from polyurethane-carbonate (PUC) polymer linings with different water permeabilities of 1,200 mL/min/cm$^2$ and 280 mL/min/cm$^2$ in an artery, indicating a wider post-implantation lumen for the stent grafts having lower water permeabilities compared to the normal-permeable prostheses at all time points (P<0.03) (published as Schurmann K, "Comparison of two stent-grafts with different porosity: in vivo studies in a sheep model," J Vasc Interv Radiol., April; 11(4):493-502 (2000)).

Preferably, the covering is formed from a polyester (e.g., polyester sold, e.g., under the trade name DACRON (E. I. DuPont De Nemours and Company), a polyurethane-carbonate (PUC) polymer, a poly(ethylene terephthalatey (PET), or poly(tetrafluoroethylene) (PTFE)) material. Other representative examples of covering materials include textiles (including, e. g., woven and non-woven materials) made from polymeric fibers. Polymeric fibers for use in textiles may be formed from a variety of polymers, including, for example, nylon and copolymers (available, e.g., under the trade name ORLON (E. I. DuPont De Nemours and Company)), polyethers or polyesters, such as polyethylene terephthalate (e.g., DACRON or MYLAR), and poly(tetrafluoroethylene) (e.g., TEFLON). Other representative examples of covering materials include non-textiles, such as polyolefins such as polypropylene, or elastomeric materials such as polyurethane or silicone rubber, and expanded polytetrafluroethylene (ePTFE).

In some embodiments, the covering material is a biocompatible polyurethane material, such as a polyureaurethane. One example of a biocompatible polyurethane is described in U.S. Pat. Application Publication No. 2002/0065552 A1 and U.S. Pat. No. 4,675,361, both of which are incorporated herein by reference, which includes, for example, a polymer blend as sold under the tradename THORALON (THORATEC, Pleasanton, Calif.). According to these patent disclosures, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer. The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

Biocompatible polyurethane materials can be formed to provide either porous or non-porous covering materials. Porous covering materials, such as THORALON, can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 30 microns to about 90 microns. The average pore diameter is measured based on images from a scanning electron microscope (SEM). Formation of porous THORALON is described, for example, in U.S. Pat. No. 6,752,826 and 2003/0149471 A1, both of which are incorporated herein by reference.

Non-porous covering materials, such as THORALON, can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

Polyurethane covering materials such as THORALON, can be used in certain vascular applications and can provide thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed in forming covering materials. These include "—C—O—N— type" (i.e., carbon-oxygen-nitrogen) polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methylpentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.). Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

Preferably, the covering material has a substantially uniform thickness. Laminar coatings of covering materials can be formed on or attached to an implantable frame to form a covering material. Preferably, coating layers have a substantially uniform thickness, with a variation of less than about 40%, preferably less than about 30%, more preferably less than about 20%, and most preferably less than about 10%.

Coatings and laminar sheets of covering materials attached to implantable frames can have any suitable thickness. For layers of covering materials, the thickness is preferably high enough to provide a desirable level of durability, but thin enough to provide an adequate level of flexibility and responsiveness to fluid contacting the valve leaflet. The thickness can be measured by any conventional technique, including a conventional micrometer. Preferably, a venous valve leaflet has a variation in thickness of about 20%, more preferably about 10%, or less.

Remodelable Materials

Preferably, a medical device can comprise a remodelable material. The remodelable material can form one or more tubular grafts contacting the outside (abluminal) and/or the interior (luminal) surface of a valve support frame, or preferably one or more valve leaflets positioned within a lumen at least partially defined by a covering material.

A variety of remodelable materials are available for use in implantable medical devices. Extracellular matrix material (ECM) is one category of remodelable materials. Naturally derived or synthetic remodelable materials can be used to provide remodelable surfaces on implantable medical devices. Remodelable materials may include or be derived from one or more of the following materials: submucosa, renal capsule membrane, dura mater, pericardium, serosa, and peritoneum or basement membrane materials. One specific example of an extracellular matrix material is small intestine submucosa (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts.

The remodelable material may comprise an extracellular matrix (ECM) material derived from a variety of suitable sources. One preferred category of ECM material is submucosal tissue. Submucosal ECM material can be obtained from any suitable source, including without limitation, intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine. More preferably, the ECM material is Tela submucosa, which is a layer of covering material-containing connective tissue occurring under the mucosa in most parts of the alimentary, respiratory, urinary and genital tracts of animals. Examples of suitable ECM materials include renal capsule matrix (RCM), urinary bladder matrix (UBM) and most preferably small intestine submucosa (SIS). Most preferably, the ECM material is obtained from processed intestinal covering material layer derived from the tunic submucosa of porcine small intestine.

One preferred remodelable material is tela submucosa, is obtained from a layer of connective tissue occurring under the mucosa in most parts of the alimentary, respiratory, urinary, integumentary, and genital tracts of animals. Tela submucosa, as with many animal tissues, is generally aseptic in its natural state, provided the human or animal does not have an infection or disease. The tela submucosa is an internal layer within the alimentary, respiratory, urinary and genital tracts of animals. Accordingly, it is generally not exposed to bacteria and other cellular debris such as the epithelium of the intestinal tract. Preferably, the tela submucosa tissue ECM materials are derived from the alimentary tract of mammals and most preferably from the intestinal tract of pigs. A most preferred source of whole small intestine is harvested from mature adult pigs weighing greater than about 450 pounds. Intestines harvested from healthy, nondiseased animals will contain blood vessels and blood supply within the intestinal tract, as well as various microbes such as *E. coli* contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

Additional information as to submucosa materials useful as ECM materials herein can be found in U.S. Pat. Nos. 4,902,508; 5,554,389; 5,993,844; 6,206,931; 6,099,567; and 6,375,989, as well as published U.S. Patent Applications US2004/0180042A1 and US2004/0137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

The ECM material such as small intestine submucosa (SIS), can be isolated from biological tissue by a variety of methods. In general, an ECM material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically, the SIS is rinsed with saline and optionally stored in a hydrated or dehydrated state until use as described below. The resulting submucosa tissue typically has a thickness of about 100-200 micrometers, and may consist primarily (greater than 98%) of acellular, eosinophilic staining (H&E stain) ECM material.

Preferably, the source tissue for the remodelable material is disinfected prior to delamination by using the preparation disclosed in U.S. Pat. No. 6,206,931, filed Aug. 22, 1997 and issued Mar. 27, 2001 to Cook et al., and US Patent Application US2004/0180042A1 by Cook et al., filed Mar. 26, 2004, published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa, e.g. by delaminating the tela submucosa from the tunica muscularis and the tunica mucosa, minimizing the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

Preferably, the ECM material is substantially free of any antibiotics, antiviral agents or any antimicrobial type agents which may affect the inherent biochemistry of the matrix and its efficacy upon implantation. An alternative to the preferred method of ECM material isolation comprises rinsing the delaminated biological tissue in saline and soaking it in an antimicrobial agent, for example as disclosed in U.S. Pat. No. 4,956,178. While such techniques can optionally be practiced to isolate ECM material from submucosa, preferred processes avoid the use of antimicrobial agents and the like which may not only affect the biochemistry of the covering material matrix but also can be unnecessarily introduced into the tissues of the patient. Other disclosures of methods for the isolation of ECM materials include the preparation of intestinal submucosa described in U.S. Pat. No. 4,902,508, the disclosure of which is incorporated herein by reference. Urinary bladder submucosa and its preparation is described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety.

Optionally, the remodelable material can be perforated, for example to promote tissue ingrowth and remodeling, for the incorporation of a bioactive material in the covering material, or for the release of a bioactive material through the covering material. In one embodiment, the remodelable material includes perforations permitting fluid movement through the wall of the medical device. Perforations in the remodelable material can be sized and configured for a desired application. For example, the perforations can be between about 10 microns to about 100 microns, preferably between about 10 microns and 60 microns, in diameter. The distribution of the perforations can be evenly spaced, such as at least about a 30-60 micron spacing over any suitable portion of the remodelable material, but preferably over at least about half of the covering material surface. Perforations may be formed in the remodelable material by any suitable means, including mechanical or laser methods, or a porous covering material can be used.

For layers of remodelable materials, the thickness is preferably high enough to provide a desirable level of durability, but thin enough to provide an adequate level of flexibility and responsiveness to fluid contacting the valve leaflet. For venous valves comprising remodelable material leaflets, the leaflet preferably has a thickness of between about 0.0001 inch and about 0.0030 inch, and more preferably about 0.0005 inch thick. The thickness can be measured by any conventional technique, including a conventional micrometer. Preferably, a venous valve leaflet has a variation in thickness of about 20%, more preferably about 10%, or less.

Support Frame Configurations

The medical device can include one or more support frames having any suitable configuration. In some embodiments, the medical device can include a first support frame attached to the covering material and a second support frame enclosed by the covering material. The remodelable material can be attached to the second support frame and/or the first support frame. In some preferred embodiments, the medical device comprises a covering material defining a cylindrical lumen and attached to a first support frame configured as a plurality of interconnected undulating hoops. A valve including a second frame and one or more valve leaflets formed from a remodelable material can be enclosed within the covering material.

Preferably, the medical device includes a first intraluminally implantable frame comprising one or more undulating ring members, optionally connected by longitudinal support members. The frame can function as a support frame for an attached covering material. In one embodiment, the covering material is positioned on the exterior (abluminal) side of the medical device. A medical device can also include a second frame positioned within the covering material and attached to the remodelable material. The second support frame can have a configuration adapted to maintain the remodelable material in a desired orientation with respect to the covering material and/or with respect to the direction of fluid flow within a body vessel.

A first or a second support frame can have any suitable configuration, but is preferably shaped and configured to maintain a covering material in a desired configuration or orientation within the body vessel. In some embodiments, the frame comprises a plurality of interconnected struts and bends, which can be of any suitable structure or orientation. In one embodiment, the frame comprises a plurality of struts connected by alternating bends. For example, the frame can be a sinusoidal ring member comprising a series of struts in a "zig-zag" or sinusoidal pattern. The frame can also comprise multiple ring members with struts in a "zig-zag," also called hoops with an undulating configuration or sinusoidal pattern. A support frame can include multiple zig-zag hoops connected end to end, or in an overlapping fashion. In some embodiments, the struts are substantially aligned along the surface of a tubular plane, substantially parallel to the longitudinal axis of the support frame.

Other examples of suitable frame shapes for support frames connected to the remodelable material, or the covering material, are provided in U.S. Pat. Nos. 6,508,833 and 6,200,336 to Pavcnik, and U.S. patent applications Ser. No. 10/721582, filed Nov. 25, 2003; 10/642,372, filed Aug. 15, 2003; and 10/294,987, filed Nov. 14, 2002, all of which are incorporated herein by reference in their entirety. Other suitable frame structures can be selected from implantable frame structures disclosed in U.S. Pat. Nos. 6,730,064; 6,638,300; 6,599,275; 6,565,597; 6,530,951; 6,524,336; 6,508,833; 6,464,720; 6,447,540; 6,409,752; 6,383,216; 6,358,228; 6,336,938; 6,325,819; 6,299,604; 6,293,966; 6,200,336; 6,096,070; 6,042,606; 5,800,456; 5,755,777; 5,632,771; 5,527,354; 5,507,771; 5,507,767; 5,456,713; 5,443,498; 5,397,331; 5,387,235; 5,530,683; 5,334,210; 5,314,472;

5,314,444; 5,282,824; 5,041,126; and 5,035,706; all assigned to Cook Inc. and incorporated in their entirety herein by reference.

Alternatively, in other embodiments, the graft material can be formed from a self-supporting material. For example, in one embodiment, the medical device comprises a rigid or flexible polymer tube positioned around an implantable valve.

Support Frame Materials

A support frame can be formed from or coated with other metal or non-metal materials. In some embodiments, a support frame can be formed from a biocompatible metal such as nitinol, cobalt-chromium or stainless steel, optionally coated with a polymer and/or a bioactive material. Examples of materials that can be used to form a frame, or can be coated on a frame, include biocompatible metals or other metallic materials, stainless steels (e.g., 316, 316L or 304), nickel-titanium alloys including shape memory or superelastic types (e.g., nitinol or elastinite), noble metals including platinum, gold or palladium, refractory metals including tantalum, tungsten, molybdenum or rhenium, stainless steels alloyed with noble and/or refractory metals, silver, rhodium, inconel, iridium, niobium, titanium, magnesium, amorphous metals, plastically deformable metals (e.g., tantalum), nickel-based alloys (e.g., including platinum, gold and/or tantalum alloys), iron-based alloys (e.g., including platinum, gold and/or tantalum alloys), cobalt-based alloys (e.g., including platinum, gold and/or tantalum alloys), cobalt-chromium alloys (e.g., elgiloy), cobalt-chromium-nickel alloys (e.g., phynox), alloys of cobalt, nickel, chromium and molybdenum (e.g., MP35N or MP20N), cobalt-chromium-vanadium alloys, cobalt-chromium-tungsten alloys, platinum-iridium alloys, platinum-tungsten alloys, magnesium alloys, titanium alloys (e.g., TiC, TiN), tantalum alloys (e.g., TaC, TaN), L605, and magnetic ferrite.

The frame can optionally be coated with one or more materials, such as biocompatible polymers. One preferred example of a polymeric coating comprises a poly(styrene-b-isobutylene-b-styrene) block copolymer deposited on a 1,3-di(2-methoxy-2-propyl)-5-tert-butylbenzene. Other suitable coatings are N-(3,4-dimethoxycinnamoyl)anthranilic acid, and phosphorylcholine. In one embodiment, the frame can comprise silicon-carbide (SiC). For example, published U.S. Patent Application No. US2004/034409 to Hueblein et al., published on Feb. 14, 2004 and incorporated in its entirety herein by reference, discloses various suitable frame materials and configurations.

Attachment of Materials

The remodelable material and covering material can be attached to each other or to the same or different support frames in any suitable manner. For example, the covering or remodelable material can be sewn or welded to the support frame (e.g., by the application of localized heat and pressure), or the application of an adhesive. The material can be attached to the support frame by the use of a small swatch of material placed on the outside of the support frame. A material positioned on the luminal or inner surface of the support frame, may be bonded to the material in a variety of ways. Among these are suturing, gluing and heat welding. In one embodiment, a covering material or remodelable material formed as a sleeve can be extended over one or both ends of a tubular support frame to form a "cuff." Cuffs can be sutured to the support frame, sutured from one cuff to the other, or otherwise bonded to the support frame or to another material positioned on the other side of the support frame. Sutures can also be used to connect the covering material and remodelable material to a support frame and/or each other. U.S. patent application Ser. No. 11/038,567, filed Jan. 18, 2005 by Lad et al., published as US2005/0159804A1 and incorporated herein by reference, discloses various attachment structures suitable for attaching a covering material to a remodelable material, or attaching either material to a support frame using sutures. Preferred suture materials for the attachment of a covering material to itself to form a tubular configuration include 5-0 sized polymer sutures, such as polyvinyl sutures; suture materials for attachment of the support frame to the covering material include 6-0 sized polymer sutures (including polypropylene); and suitable materials for attachment of the valve structure to a covering material include 7-0 sized polymer sutures, such as polypropylene sutures. Preferably, the sutures are not biodegradable.

The covering material or remodelable materials ("materials") may be attached to the support frame by any of several design features which may be incorporated into the support frame. Materials may also be attached to the support frame by providing a porous or perforated support frame or materials, thus allowing the support frame to act as a forming mandrel for materials. By providing a support frame with hooks, or other similar topography, the sleeve may be readily attached to the support frame. The sleeve material may be impaled on such barbs, thus securing the sleeve. With hooks of the appropriate size, the materials may not be perforated, but rather embedded in the holding topography. Frame structures for attaching a support frame to a covering material or remodelable material are described in U.S. patent application Ser. No. 11/056,675, filed Feb. 11, 2005 by Osborne et al., published as US2005/0149167A1 on Jul. 7, 2005 and incorporated herein by reference, are also suitable as a means for attaching the remodelable material to the covering material.

The covering material can also be precipitated onto the support frame by heating the support frame in a solution of covering material. The covering material can form a matrix on the surface of the support frame, then when properly annealed, the covering material can form a fibular, well organized structure conducive for the attachment and growth of cells. For example, a covering material can be cast inside a support frame in a manner described in U.S. Pat. No. 5,693,085, to Buscemi et al., issued Dec. 2, 1997, which is incorporated herein by reference. Thus, the covering material may be coated onto the support frame surfaces as desired by spraying or dip coating or electrodeposition or the like or attached in other ways as described above. Such a coating might be about 1-50 microns thick. A covering material coated support frame may also have a covering material over the covering material coating or under the covering material coating. The inside of the support frame may then be coated with covering material. Preferably, in such an arrangement, the sleeve will be SIS. It is also possible in the case of an open-work support frame, to coat the support frame struts with covering material, place a covering material either over or inside the support frame, or both, and then heat bond the sleeve and/or covering material to the coating. This would preferably be done with collagen-based covering material, especially SIS or with fibrin.

Preferably, remodelable material is oriented on the support frame when the remodelable material is used in the form of an ECM sheet which is wrapped around the support frame or a tube inserted in the support frame. ECM sheet remodelable material can be stretched, however its stretchability is predominantly unidirectional. ECM remodelable material sheet, when used as a sleeve or remodelable material on a support frame which undergoes expansion and/or contraction, can be attached to the support frame on a "bias," in a manner described in U.S. Pat. No. 5,693,085, to Buscemi et al., issued Dec. 2, 1997, which is incorporated herein by reference. Briefly, the ECM remodelable material sheet can be oriented at a 45 degree angle relative to the longitudinal axis of a tubular support frame.

Incorporation of Bioactive Materials

Optionally, one or more bioactives can be included in a covering material, a remodelable material or a support frame. The bioactive material can be selected to treat indications such as coronary artery angioplasty, renal artery angioplasty, carotid artery surgery, renal dialysis fistulae stenosis, or vascular graft stenosis. One or more bioactives can be coated on or incorporated within a support frame, remodelable material or covering material by any suitable technique. In one embodiment, a remodelable material, a covering material or support frame can be configured to absorb a solution of a bioactive material. For instance, a covering material with absorbent properties can be selected, or a portion of a medical device can be coated with a cross-linked polymer hydrogel material to retain a bioactive material for elution within a body vessel. A bioactive can be incorporated by soaking the absorbent portion of the medical device in a solution of the bioactive material and allowing the absorption of the bioactive solution. Subsequently, the solvent can be evaporated to leave the bioactive within the medical device.

In one embodiment, the frame is coated with a coating of between about 1 µm and 50 µm, or preferably between 3 µm and 30 µm, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. patent application Ser. No. 10/639,225, filed Aug. 11, 2003 and published as US2004/0034409A1 on Feb. 19, 2004, describes methods of coating a support frame with bioabsorbable materials such as poly-L-lactic acid that are incorporated herein by reference.

Bioactive material can be placed within or on the porous remodelable material. Alternatively, bioactive material can elute from a support frame or an underlying covering material, through the porous covering material. The rate at which the bioactive material passes through the porous covering material is determined by several factors, including the size and number of the pores and the size, charge and polarity of the bioactive material molecules. In some applications it may be desirable to include perforations in the support frame, remodelable and/or covering materials to provide elution of a bioactive during fluid permeation or movement through a portion of the medical device. Such an arrangement is readily obtained as support frames are generally open or perforate with respect to their structure and perforations may be readily formed in a material, the perforations extending through the support frame openings. Perforation in materials of about 10-60 microns in diameter may be desirable for some applications. The distribution of the perforations may be such as to be evenly spaced, such as at 30-60 micron spacing and to occupy about one-half of the material surface areas.

Bioactive materials can be attached to the medical device in any suitable manner. For example, a bioactive can be attached to the surface of the medical device, or be positioned within the support frame, remodelable material or covering material in pores. Referring again to FIG. 1A, one or more bioactive agents can be coated on or impregnated in the support frame 40, the covering material 30 or the remodelable material 20. The bioactive agent can be selected to perform one or more desired biological functions. An anti-angiogenic or antineoplastic bioactive such as paclitaxel, sirolimus or a rapamycin analog, or a metalloproteinase inhibitor such as batimastaat can be incorporated or coated on a support frame or material to mitigate or prevent undesired conditions in the vessel wall, such as restenosis. Many other types of bioactive agents can be incorporated in a remodelable material, covering material or a support frame.

Bioactive materials for use in bio-compatible coatings include those suitable for coating on an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

A bioactive material can be one or more pro-healing therapeutic agents, which include materials that provide or promote endothelial cell seeding. For instance, coatings comprise antibodies to CD34 receptors on progenitor circulating endothelial cells. Nitric oxide, vascular endothelial growth factor, and 17-β-estradiol are other examples of prohealing therapeutic agents. Another prohealing bioactive agent is vascular endothelial growth factor (VEGF). VEGF is an endothelial cell-specific mitogen, and a cytokine involved in processes essential to the growth, maintenance and repair of vascular structures. VEGF can be coated on an implantable frame, an attached material, or both. Local drug delivery of VEGF from a medical device, such as a stent frame, can reduce in-stent restenosis. Other examples of pro-healing therapeutic agents, along with methods for coating the same on implantable medical devices, are provided in published U.S. Patent Application Nos. 2005/0092440 (filed Nov. 8, 2002, by Weinstein); 2005/0191333 (filed Apr. 28, 2005 by Hsu); and 2005/0148585 (filed Aug. 26, 2004 by Davies et al.), which are incorporated herein by reference.

Medical devices comprising an antithrombogenic bioactive material are particularly preferred for implantation in areas of the body that contact blood. An antithrombogenic bioactive material is any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus. Examples of anti-thrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive materials include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells.

Methods of Manufacture

Other embodiments provide methods of making medical devices described herein. Methods of manufacturing medical devices can include the steps of: positioning a sleeve of a covering material around an implantable valve, attaching a covering material to a support frame, attaching a remodelable material to a support frame to form an implantable valve, and attaching a remodelable material to the covering material. The implantable valve preferably includes a remodelable material forming a valve leaflet.

In one embodiment, a covering material is attached to a portion of a support frame using stitching through the covering material and around a portion of the support frame, adhesives, tissue welding or cross linking to directly join the covering material to the frame. A remodelable material is preferably used to form a valve leaflet optionally attached to a valve support frame so as to move relative to the support frame, or the valve leaflet can be substantially fixed in its position or orientation with respect to the support frame by using attachment configurations that resist relative movement of the leaflet and the support frame.

Medical devices comprising a covering material formed from a biocompatible polyurethane based polymer as described above, including materials sold under the tradename THORALON, can be attached to an implantable support frame by various methods. In some embodiments, a polyurethane covering material can be formed by drying a solution of the dissolved covering material on a surface with a desired shape. In one embodiment, the dried covering material can be adhered to a support frame using an adhesive, sutures, UV-activated polymers, melting, or any suitable means of attachment providing a desirably durable attachment between the covering material and the implantable frame. Preferably, a solution of the dissolved covering material can be coated onto a portion of the frame and attached to the frame as the solution is dried.

The solution comprising a dissolved covering material is coated and dried on a mandril to form a covering material. Preferably, the covering material is a non-porous THORALON material. A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethylacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandril or a mold.

Covering material layers can be sewn onto a frame or around a valve, or can be formed by applying one or more layers of the solution of the dissolved covering material composition to a mandril and/or to an assembly comprising an implantable support frame fitted over a mandril, and then drying the applied solution to remove excess volatile solvent and to solidify the solution coating to form one or more portions of the covering material. When applied to a mandril alone, the dried covering material can be separated from the mandril and attached to an implantable frame. Alternatively, an implantable frame can be fitted over a mandril that has been pre-coated with a layer of the covering material, and additional layers of the dissolved covering material can be applied to the frame and pre-coated mandril together. The additional layers can adhere to or combine with the pre-coating layer on the mandril to surround portions of the implantable frame, thereby securing a portion of the coating of covering material to the enclosed portions of the implantable frame. The mandril can be made from any suitable material that permits the covering material to coated, dried on and removed from the mandril surface. Suitable materials include stainless steel and glass. Preferably, at least a portion of the outer surface of the mandril is formed in the desired shape of a covering material sleeve. The covering material sleeve can be formed by coating a thin layer of a solution of the covering material onto the mandril, drying the coating of the covering coating on the mandril surface, and carefully removing the covering material as a tube or sleeve. Optionally, a support frame can be placed over the mandril and sprayed with the covering material to form a sleeve adhered to the support frame. Alternatively, a valve comprising a remodelable valve leaflet can be placed over the mandril, and a covering material can be sprayed over the valve to form a covering material configured as an outer sleeve around the valve.

For example, a solution of covering material can be a solution of non-porous THORALON sprayed from a spray gun onto the mandril to form a substantially uniform coating layer over a tapered portion of the mandril. Preferably, the mandril is rotated during spraying process to promote uniform coating of the mandril. Any suitable rate of rotation can be used. Factors such as the temperature, viscosity and spray pressure can be considered in optimizing the rotation rate and spraying process. For example, a typical rotation rate of about 5 rpm can be used. The solution of covering material is coated onto the surface of the distal end of the mandril and dried to form an article of manufacture substantially conforming to the shape of the tapered portion. Optionally, one or more bioactive agents can be coated onto the mandril with the covering material.

Alternatively, coating layers can be formed by dipping a support frame and/or a valve into a solution of the covering material to attach the covering material. During the dipping of the mandril or the assembly, the mandril can be rotated before, during and after contact with the solution of covering material. To provide a more uniform coating of covering material on the mandril and attached to the frame, the following parameters of the dipping process can be varied: the temperature of the mandril, the rate and direction of rotation of the mandril, the rate of dipping, the time the mandril coating surface is maintained in the solution of covering material, and the viscosity of the solution.

The coating surface on the mandril and/or frame can optionally be heated before, during or after coating with the covering material. Preferably, the solution and coating surface are at a similar or the same temperature. The mandril and solution can be maintained at any temperature that maintains the solution in a liquid state with a desired level of viscosity. For THORALON polyureaurethane materials, a mandril temperature of about 50° to about 60° C. is preferred for the dip coating process, preferably about 55° C.

The coating surface can be spun at any suitable rate before, during or after contact with the solution of covering material. The mandril can be spun clockwise, counter-clockwise or the rotation can be reversed once or more at any point during the coating or drying process. For THORALON polyurethaneurea covering materials, the coating surface of a mandril or assembly can be rotated between about 1 rpm to about 120 rpm in a clockwise direction going into the solution, and a counterclockwise direction during removal from the solution and during drying. The rate of rotation can depend on the viscosity of the solution. Generally, the higher the viscosity of the solution, the faster the mandril is spun while in contact with the solution, to promote more uniformity in coating thickness over the coating surface. A slower rotation rate can be employed in a solution with a lower viscosity. The viscosity of the solution of covering material can be varied, depending on the desired composition of the material. Generally, solution viscosities of between about 200 to 20,000 centipoise are suitable for coating a mandril or assembly, preferably between about 600 and 1,000 centipoise.

During the dipping process, the mandril can be translated into the solution of covering material at any rate that promotes desirable properties of the coating of covering materials. The rate of translation into or out of the solution can be the same or different. For THORALON polyurethaneurea covering materials, preferred translation rates for movement of the coating surface into or out of the solution correspond movement of 1 inch of length of coating surface with respect to the surface of the solution in a time between about 2 to about 20 seconds, depending on the viscosity and composition of the solution. Preferably, the rate of translation of the coating surface is slower going into the solution and faster exiting the solution.

Optionally, the coating surface on the mandril or frame can remain in the solution for a suitable dwell time. The coating surface can be stationary or can be rotated during all or part of the dwell time. For THORALON polyurethaneurea covering materials, preferred dwell times are between 1 second and 1 minute, while rotating the coating surface in the solution.

When a coating surface is dipped multiple times in the solution, the coated surface of the mandril, frame or assembly, is preferably briefly dried for an intermittent drying time of about 1 minute to about 1 hour, to remove some removing excess volatile solvent. For THORALON polyurethaneurea covering materials dissolved in dimethyacetamide solvent, the coating surface is preferably maintained at a drying temperature of about 40° C. to about 60° C. during the intermittent drying period. Although the coating surface can be heated, other embodiments provide dipping methods without heating of the coating surface.

After applying the final coat of the solution, and removal of the coating and removal from the solution, the coated surface of the mandril, frame or assembly, is preferably dried by removing excess volatile solvent. The coated surface can be dried in a heat chamber, and maintained at a suitable temperature for a suitable period of time to remove excess solvent and dry the coating. The drying temperature can be set suitably high to evaporate excess solvent from the coating, and can depend on the solvent used in the solution. Preferably, the drying temperature is substantially the same as the temperature of the solution and/or the mandril. For THORALON polyurethaneurea covering materials dissolved in dimethyacetamide solvent, the final medical device comprising the THORALON material attached to a frame is preferably maintained at a drying temperature of about 40° C. to about 60° C. for a period of between about 1 minute to about 24 hours to evaporate, more preferably between about 1 hour and 24 hours.

After the coating and dipping processes are completed, the coated device can be dried for about 8 hours at a temperature of about 60° C. to remove excess solvent and to solidify the leaflets and the leaflet attachment to the frame. After drying, the medical device can be removed from the mandril, for example by inserting a fine gauge needle between the dried covering material and the mandril coating surface and injecting a small volume of water to promote separation of the covering material from the mandril.

Alternatively, a covering material can be formed from a sheet of polyureaurethane material attached to the frame by other methods. In one embodiment, a sheet of covering material is cut to a desired dimension is wrapped around portions of a support frame and portions of the covering material sealably connected together to fasten the covering material around the frame. For example, one edge of a sheet of covering material can be wrapped around a portion of the support frame and held against the body of the covering material, so that the covering material forms a lumen enclosing the support frame portion. A small amount of a suitable solvent is then applied to the edge of the covering material to dissolve the edge into an adjacent portion of the covering material and thereby seal the material around the support frame.

Methods of Treatment

Still other embodiments provide methods of treating a subject, which can be animal or human, comprising the step of implanting one or more support frames as described herein. Other methods further comprise the step of implanting one or more frames attached to one or more graft members, as described herein. In some embodiments, methods of treating may also include the step of delivering a medical device to a point of treatment in a body vessel, or deploying a medical device at the point of treatment.

Methods of treating peripheral vascular disease, including critical limb ischemia, comprising the endovascular implantation of one or more medical devices are provided. Atherosclerosis underlies most peripheral vascular disease. Narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

The medical device can be implanted in any suitable body vessel. The configuration of the implantable frame can be selected based on the desired site of implantation. For example, for implantation in the superficial artery, popliteal artery or tibial artery, frame designs with increased resistance to crush may be desired. For implantation in the renal or iliac arteries, frame designs with suitable levels of radial force and flexibility may be desired.

In one embodiment, a medical device comprising a balloon-expandable frame portion and an attached covering material enclosing a remodelable material can be endoluminally delivered to a point of treatment within an infrapopliteal artery, such as the tibial or peroneal artery, to treat CLI. For treating focal disease conditions, balloon expandable medical devices can comprise an expandable frame attached to a coating that encloses and is attached to the frame. The frame can be configured to include a barb or other means of securing the medical device to the wall of a body vessel upon implantation.

In another embodiment, a medical device can be configured as a self-expanding device configured to provide a desirable amount of outward radial force to secure the medical device within the body vessel. The medical device can be preferably implanted within the tibial arteries for treatment of CLI. For instance, the medical device can be configured as a vascular stent having a self-expanding support frame formed from a superelastic self-expanding nickel-titanium alloy attached to a covering material. The use of a self-expanding frame can be preferably used when the body vessel to be stented extends into the distal popliteal segment. The selection of the type of implantable frame can also be informed by the possibility of external compression of an implant site within a body vessel during flexion of the leg.

Methods for delivering a medical device as described herein to any suitable body vessel are also provided, such as a vein, artery, biliary duct, ureteral vessel, body passage or portion of the alimentary canal. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

In one embodiment, a method of treating a venous valve related condition can include the step of implanting a valve within a body vessel. A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. These venous valves open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve-related conditions are chronic venous insufficiency and varicose veins.

The implantable valve can be implanted at any suitable site in the vasculature. For treatment of venous disease, the valve is desirably implanted in the deep venous or superficial venous system. Preferably, the valve is implanted percutaneously to a point of treatment in a body vessel using any suitable delivery device, including delivery catheters dilators, sheaths, and/or other suitable endoluminal devices. Alternatively, the valve can be placed in body vessels or other desired areas by any suitable technique, including percutaneous delivery as well as surgical placement. The valve advantageously has a radially compressed and a radially expanded configuration and can be implanted at a point of treatment within a body vessel by delivery and deployment with an intravascular catheter. The valve may include a support frame that may optionally provide additional function to the valve. For example, the support frame can provide a stenting function, i.e., exert a radially outward force on the interior wall of a vessel in which the valve is implanted. By including a support frame that exerts such a force, a valve can provide both a stenting and a flow-modifying function at a point of treatment within a body vessel.

Figure 6:
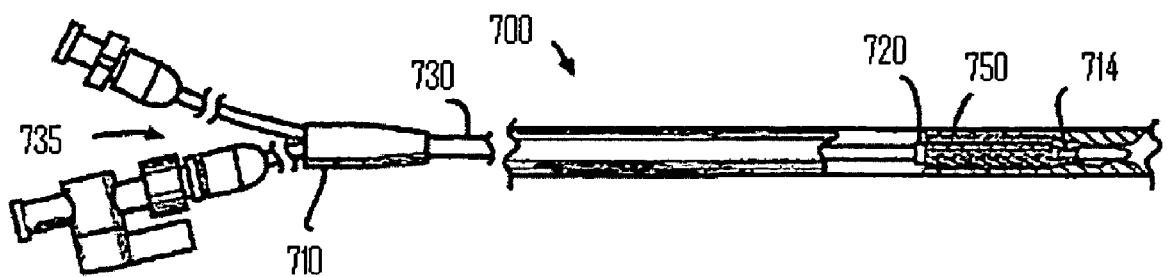
FIG. 6 shows a schematic of a delivery system comprising a catheter.

FIG. 6 illustrates a delivery system 700. The delivery system 700 includes a catheter 730 having a distal end 714. A balloon 720 is positioned on the distal end 714 of the catheter 730. A connector assembly 735 is disposed at the proximal end 710 of the catheter 730 and is adapted to facilitate expansion of the balloon 720 as is known in the art. The connector assembly 735 provides access to an interior lumen of the catheter 730 to provide access to the balloon 720, and possibly a guidewire (not illustrated) or other conventional component.

A balloon expandable frame 750 according to the present invention is disposed on the distal end 714 of the catheter 730. The medical device 750 surrounds the balloon 720 and is initially, prior to placement in a body vessel, in its unexpanded state. This positioning allows the balloon 720, upon inflation, to expand the medical device 750 into its expanded state. An implantable medical device comprising a radially expandable support frame can support a body vessel. This can be performed by inserting the distal end 714 of the catheter 730 into a body vessel and navigating the distal end 714, and the surrounding medical device 750, to a point in a vessel. The catheter 730 can be placed over a guidewire (not illustrated) to facilitate navigation. Once the medical device 750 is at the point of treatment, the balloon 720 can be inflated in the conventional manner. Inflation of the balloon 720 forces the medical device 750 to expand. Following expansion, the balloon 720 can be deflated, leaving the medical device 750 in its expanded state. The catheter 730 can then be withdrawn from the vessel, leaving the medical device 750 in its expanded state at the point of treatment within the body vessel.

An appropriately sized delivery catheter can be selected by one skilled in the art for a given application. For example, some embodiments can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 french (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 F (1.10 mm) delivery catheters.

Medical devices can be delivered into a body lumen using a system which includes a catheter. In some embodiments, medical devices can be intraluminally delivered inside the body by a catheter that supports the medical device in a compacted form as it is transported to the desired site, for example within a body vessel. Upon reaching the site, the medical device can be expanded and securably placed within the body vessel, for example by securably engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the medical device is formed of an elastic material that will self-expand after being compacted. During introduction into the body, the medical device is restrained in the compacted condition. When the stent has been delivered to the desired site for implantation, the restraint is removed, allowing the medical device to self-expand by its own internal elastic restoring force. Once the medical device is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

In some embodiments, the medical devices impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed force does not traumatize the lumen walls.

The medical devices can be placed in any medically appropriate location for a given application. For example, in some embodiments, the medical device can serve as part of a venous valve prosthetic and be implanted in the femoral vein, including at the proximal (groin), mid (mid section) or distal (adjacent to the knee) portions of the vein.

EXAMPLES

Example 1

Medical Device Comprising a Valve and PET Covering Material

Various medical devices were prepared by the following steps:
1. providing a self-expanding nickel-titanium (NITINOL) valve support frame defining a cylindrical lumen with a plurality of openings, having an outer diameter of 12 mm or 14 mm;
2. attaching two opposable valve leaflets formed from small intestine submucosa (SIS) to the support frame to form a bicuspid valve;
3. enclosing the bicuspid valve from step (2) in a sheet of poly(ethylene terephthalate) (PET) covering material having a thickness of about 0.12 mm; the covering material had a length of 40 mm for the medical device comprising the 12 mm diameter valve frame and a length of 45 mm for the medical device comprising the 14 mm diameter valve frame;
4. securing the covering material to itself to form a tube by joining overlapping ends of the covering material to each other with 5-0 polyvinyl braided sutures;
5. attaching the valve frame to the covering material using 7-0 monofilament polypropylene sutures;
6. placing two sinusoidal ring members around the covering material, with one ring member at the proximal end of the covering material and the other ring member around the base of each valve leaflet; each ring member having 8 struts connected by a plurality of single bends;
7. attaching each ring member to the covering material using 6-0 monofilament polypropylene sutures; and
8. radially compressing the medical device by crimping to a size suitable for delivery in a 12-french inner diameter delivery catheter.

Example 2

Medical Device Comprising a Valve and Polyurethane Covering Material

Various medical devices may be prepared by the following steps:
1) Forming a tubular sleeve of THORALON polyurethane material attached to a series of coaxially-aligned ring members by the following steps
　a) about 10 mL of a THORALON/DMAC polyurethane solution was prepared with a weight ratio of solid (BPS-215 and SMA-300, and optionally containing a salt for forming the porous THORALON material) to DMAC of between about 1:1.5 to about 2:1;
　b) a glass tube was cleaned with soap and water, and about 2 mL of the solution was applied uniformly to the inside of the glass tube;
　c) the coated glass tube was heated while rotating the tube slowly about the longitudinal axis (ca. 5 rpm) for about 2 hours at about 40 deg. C.;
　d) the coated glass tube is cooled to room temperature and multiple self-expanding ring members were deployed within the coated glass tube;
　e) about 2 mL of the solution was applied uniformly to the inside of the glass tube and around the ring members;
　f) the coated glass tube and ring members was heated while rotating the tube slowly about the longitudinal axis (ca. 5 rpm) for about 2 hours at about 40 deg. C.;
　g) the dried covering material sleeve structure containing the ring members was removed from the glass tube and soaked in a warm water bath at a temperature of about 65 deg. C. for about 1 hour, then removed and dried;
2) a self-expanding valve comprising remodelable leaflets is formed by the following steps:
　a) providing a self-expanding nickel-titanium (NITINOL) valve support frame defining a cylindrical lumen with a plurality of openings, having an outer diameter of 14 mm or 16.5 mm;
　b) radially compressing the frame to an outer diameter of 12 mm (for 14 mm frame) or 14 mm (for 16.5 mm frame);
　c) attaching two opposable valve leaflets formed from small intestine submucosa (SIS) to the support frame in a manner that the attached leaflets maintain the frame in the radially compressed state of step (2)(b) above, the leaflets also being attached in a manner providing that at least a portion of each of the attached valve leaflets are opposable to one another to create a valve orifice functioning as a bicuspid valve; the valve orifice is configured to permit fluid flow in an antegrade direction while substantially preventing retrograde fluid flow; the leaflet material is selected to permit the valve orifice to open and close by movement of the valve leaflet material in response to fluid contacting the leaflets, without requiring hinged movement of the frame to open and close;
3) radially compressing the valve from step 2, placing the radially compressed valve in the lumen of the covering material sleeve in step 1 and deploying the valve from step 2 within the lumen of the covering material sleeve;

4) optionally, the valve may be attached to the covering material by suturing or adhesive bonding; and 5) optionally, radially compressing the medical device by crimping to a size suitable for delivery in a 10-12-french inner diameter delivery catheter.

The invention includes other embodiments within the scope of the claims, and variations of all embodiments, and is limited only by the claims made by the Applicants.

We claim:

1. An implantable radially expandable medical device moveable from a radially compressed state to a radially expanded state, and having an interior surface defining an interior lumen and an exterior surface, the medical device comprising:

a substantially non-remodelable covering material configured as a first tubular sleeve having a first abluminal side defining at least a first portion of the exterior surface of the medical device and a first luminal side defining a first portion of the interior surface of the medical device;

a remodelable material configured as a second tubular sleeve and positioned concentrically within the covering material, the remodelable material having a second abluminal side and a second luminal side defining a second portion of the interior surface of the medical device; and a radially expandable support frame attached to the abluminal side of the covering material and defining at least a second portion of the exterior surface of the medical device, the radially expandable support frame defines a proximal portion comprising a proximal flared end of the support frame, a distal portion comprising a distal flared end of the support frame, and an intermediate portion extending along the entire axial length between the proximal and distal flared ends and comprising a connecting member extending between and connecting the proximal and distal flared ends, each of the proximal and distal flared ends having an outer diameter that is greater than the outer diameter of the intermediate portion when the medical device is in the radially expanded state;

wherein the covering material comprises a second proximal flared end and a second distal flared end and extends longitudinally from a point in the proximal flared end of the support frame, through the intermediate portion and to a point in the distal flared end of the support frame such that the second proximal flared end is disposed radially within the proximal flared end of the support frame and the second distal flared end is disposed radially within the distal flared end of the support frame;

wherein the remodelable material extends along the entire length of the intermediate portion of the support frame and does not extend into the proximal or distal portions of the support frame;

wherein the first and second portions of the interior surface of the medical device are exposed to fluid flow when the medical device is placed within a body vessel and expanded to the radially expanded state.

2. The medical device of claim 1, wherein the covering material comprises a material selected from the group consisting of: poly(ethylene terephthalate) (PET), polyester, poly (tetrafluoroethylene), nylon, polyurethane, expanded polytetrafluoroethylene (ePTFE), and copolymers thereof.

3. The medical device of claim 1, wherein the covering material comprises poly(ethylene terephthalate) (PET) or polyester.

4. The medical device of claim 1, wherein the support frame comprises a nickel-titanium alloy or stainless steel.

5. The medical device of claim 1, wherein the support frame includes a plurality of ring structures attached to the abluminal side of the covering material; the ring structures each comprising a serpentine configuration of struts and bends forming the ring structure.

6. The medical device of claim 5, wherein the medical device further comprises a valve attached to the covering material and positioned at least partially within the interior lumen of the medical device the valve comprising a valve leaflet comprising the remodelable material; and wherein the valve is positioned between a first ring structure and a second ring structure of the plurality of ring structures, the first ring structure and the second ring structure independently attached to the abluminal side of the covering material.

7. The medical device of claim 1, wherein the medical device further comprises a valve means positioned at least partially within the interior lumen of the medical device, the valve means comprising a valve leaflet comprising the remodelable material.

8. The medical device of claim 7, wherein the remodelable material is an extracellular matrix material.

9. The medical device of claim 7, wherein the valve means comprises a first valve leaflet including a first valve leaflet free edge and a first portion of the remodelable material attached to a valve support frame, wherein the valve support frame is positioned within the portion of the interior lumen defined by the covering material.

10. The medical device of claim 9, wherein the valve means further comprises a second valve leaflet defining a second valve leaflet free edge and comprising a second portion of the remodelable material attached to the valve support frame; wherein the second valve leaflet free edge is positioned in opposition to the first valve leaflet free edge to cooperatively define at least a portion of a valve orifice, the first valve leaflet and the second valve leaflet comprising flexible portions moveable in response to fluid within the interior lumen so as to permit fluid to flow in a substantially unidirectional manner through the valve orifice within the interior lumen.

11. The medical device of claim 7, wherein the valve means comprises two or more valve leaflets attached to a valve support frame, wherein each leaflet extends from a flexible free edge and a leaflet base edge distal to the flexible free edge, the leaflet base edge being attached to the valve support frame and the leaflet free edge moveable relative to the valve support frame; a. wherein at least a portion of each leaflet base edge is also attached to the covering material and each leaflet free edge is moveable relative to the covering material; b. where the implantable valve comprises a valve orifice defined by at least two flexible leaflet free edges, where the valve orifice permits fluid to flow in a first direction through the implantable valve when each valve leaflet is in the open position, and where each leaflet free edge is moveable in response to fluid flow contacting the leaflet free edge.

12. The medical device of claim 11, wherein each valve leaflet has (n) edges and (n−1) edges of each valve leaflet contact the covering material to form a sinus region between the valve leaflet and the covering material; where (n) is an integer equal to 2 or greater.

13. The medical device of claim 7, wherein the valve means comprises a tubular body formed from the remodelable material, positioned within the covering material defining a cylindrical interior lumen extending between a tapered end and a non-tapered end; where the tapered end comprises a flexible valve orifice moveable between an open position permitting fluid flow in a first direction through the interior lumen and a closed position substantially preventing fluid flow into the interior lumen, the valve orifice moveable in response to fluid flow contacting the tapered end.

14. An implantable radially expandable medical device moveable from a radially compressed state to a radially expanded state, and having an interior surface defining an interior lumen and an exterior surface, the medical device comprising:
- a substantially non-remodelable covering material configured as a first tubular sleeve having a first abluminal side defining at least a first portion of the exterior surface of the medical device and a first luminal side defining a first portion of the interior surface of the medical device;
- a remodelable material configured as a second tubular sleeve and positioned concentrically within the covering material, the remodelable material having a second abluminal side and a second luminal side defining a second portion of the interior surface of the medical device;
- a radially expandable support frame attached to the abluminal side of the covering material and defining at least a second portion of the exterior surface of the medical device, the support frame defining a proximal portion comprising a proximal flared end of the support frame, a distal portion comprising a distal flared end of the support frame, and an intermediate portion extending along the entire axial length between the proximal and distal flared ends and comprising a connecting member extending between and connecting the proximal and distal flared ends; and
- a valve means positioned at least partially within the interior lumen of the medical device, the valve means comprising a valve leaflet comprising the remodelable material;
- wherein the covering material comprises a second proximal flared end and a second distal flared end and extends longitudinally from a point in the proximal flared end through the intermediate portion and to a point in the distal flared end such that the second proximal flared end is disposed radially within the proximal flared end of the support frame and the second distal flared end is disposed radially within the distal flared end of the support frame; and
- wherein the remodelable material is disposed in the intermediate portion and does not extend into the proximal or distal portions; and
- wherein the first and second portions of the interior surface of the medical device are exposed to fluid flow when the medical device is placed within a body vessel and expanded to the radially expanded state.

15. An implantable radially expandable medical device moveable from a radially compressed state to a radially expanded state, and having an interior surface defining an interior lumen and an exterior surface, the medical device comprising:
- a substantially non-remodelable covering material configured as a first tubular sleeve having a first abluminal side defining at least a first portion of the exterior surface of the medical device and a first luminal side defining a first portion of the interior surface of the medical device, the covering material defining a flared proximal end and a flared distal end;
- a remodelable material configured as a second tubular sleeve and positioned concentrically within the covering material, the remodelable material having a second abluminal side and a second luminal side defining a second portion of the interior surface of the medical device;
- a radially expandable support frame attached to the abluminal side of the covering material and defining at least a second portion of the exterior surface of the medical device, the support frame defining a proximal portion comprising a proximal flared end of the support frame, a distal portion comprising a distal flared end of the support frame, and an intermediate portion extending along the entire axial length between the proximal and distal flared ends and comprising a connecting member extending between and connecting the proximal and distal flared ends; and
- a valve means positioned at least partially within the interior lumen of the medical device, the valve means comprising a valve leaflet comprising the remodelable material;
- wherein the covering material comprises a second proximal flared end and a second distal flared end and extends longitudinally from a point in the proximal flared end through the intermediate portion and to a point in the distal flared end such that the second proximal flared end is disposed radially within the proximal flared end of the support frame and the second distal flared end is disposed radially within the distal flared end of the support frame;
- wherein the remodelable material is disposed in the intermediate portion and does not extend into the proximal or distal portions;
- wherein the flared proximal end is disposed within the proximal portion and the flared distal end is disposed within the distal portion; and
- wherein the first and second portions of the interior surface of the medical device are exposed to fluid flow when the medical device is placed within a body vessel and expanded to the radially expanded state.

* * * * *